(12) United States Patent
Garrison et al.

(10) Patent No.: US 12,249,346 B2
(45) Date of Patent: Mar. 11, 2025

(54) METHOD FOR DETECTING AND CLASSIFYING COUGHS OR OTHER NON-SEMANTIC SOUNDS USING AUDIO FEATURE SET LEARNED FROM SPEECH

(71) Applicant: Google LLC, Mountain View, CA (US)

(72) Inventors: Jacob Garrison, Seattle, WA (US); Jacob Scott Peplinski, Chandler, AZ (US); Joel Shor, Tokyo (JP)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 18/509,722

(22) Filed: Nov. 15, 2023

(65) Prior Publication Data

US 2024/0161769 A1    May 16, 2024

Related U.S. Application Data

(63) Continuation of application No. 17/507,461, filed on Oct. 21, 2021, now Pat. No. 11,862,188.
(Continued)

(51) Int. Cl.
*G10L 25/66* (2013.01)
*A61B 5/00* (2006.01)
(Continued)

(52) U.S. Cl.
CPC ............ *G10L 25/66* (2013.01); *A61B 5/0823* (2013.01); *A61B 5/4803* (2013.01);
(Continued)

(58) Field of Classification Search
CPC ....... A61B 5/0823; G10L 25/66; G10L 25/51; G10L 25/30
See application file for complete search history.

(56) References Cited

U.S. PATENT DOCUMENTS 6,436,057 B1   8/2002   Goldsmith et al.
8,777,874 B2   7/2014   Zhang et al.
(Continued)

FOREIGN PATENT DOCUMENTS

WO    WO-2019084419 A1 *   5/2019   ............... G06N 3/04

OTHER PUBLICATIONS

Amoh et al., "Deep Neural Networks for Identifying Cough Sounds," IEEE Transactions on Biomedical Circuits and Systems, 2016, 9 pages, vol. 10, No. 5.
(Continued)

*Primary Examiner* — Samuel G Neway
(74) *Attorney, Agent, or Firm* — McDonnell Boehnen Hulbert & Berghoff LLP

(57) ABSTRACT

A method of detecting a cough in an audio stream includes a step of performing one or more pre-processing steps on the audio stream to generate an input audio sequence comprising a plurality of time-separated audio segments. An embedding is generated by a self-supervised triplet loss embedding model for each of the segments of the input audio sequence using an audio feature set, the embedding model having been trained to learn the audio feature set in a self-supervised triplet loss manner from a plurality of speech audio clips from a speech dataset. The embedding for each of the segments is provided to a model performing cough detection inference. This model generates a probability that each of the segments of the input audio sequence includes a cough episode. The method includes generating cough metrics for each of the cough episodes detected in the input audio sequence.

22 Claims, 16 Drawing Sheets

Related U.S. Application Data

(60) Provisional application No. 63/104,291, filed on Oct. 22, 2020.

(51) Int. Cl.

| | | |
|---|---|---|
| *A61B 5/08* | (2006.01) | |
| *G10L 15/02* | (2006.01) | |
| *G10L 15/04* | (2013.01) | |
| *G10L 15/06* | (2013.01) | |
| *G10L 25/30* | (2013.01) | |
| *G10L 25/51* | (2013.01) | |
| *G10L 25/78* | (2013.01) | |
| *G16H 40/67* | (2018.01) | |

(52) U.S. Cl.
CPC .......... *A61B 5/7267* (2013.01); *A61B 5/7282* (2013.01); *G10L 15/02* (2013.01); *G10L 15/04* (2013.01); *G10L 15/063* (2013.01); *G10L 25/30* (2013.01); *G10L 25/51* (2013.01); *G10L 25/78* (2013.01); *G16H 40/67* (2018.01)

(56) References Cited

U.S. PATENT DOCUMENTS

| | | | |
|---|---|---|---|
| 9,526,458 | B2 | 12/2016 | Macauslan |
| 10,448,920 | B2 | 10/2019 | Patel et al. |
| 11,862,188 | B2 * | 1/2024 | Garrison ............... A61B 5/7267 |
| 2012/0265024 | A1 * | 10/2012 | Shrivastav ............ G16H 50/30 600/300 |
| 2015/0073306 | A1 * | 3/2015 | Abeyratne ............ G16H 50/30 600/586 |
| 2015/0245788 | A1 | 9/2015 | Schmidt |
| 2018/0035901 | A1 * | 2/2018 | Cronin ..................... A61B 5/00 |
| 2020/0015709 | A1 * | 1/2020 | Peltonen .............. A61B 5/7267 |
| 2020/0029929 | A1 | 1/2020 | Patel et al. |
| 2020/0060604 | A1 | 2/2020 | Mohammadi et al. |
| 2020/0098384 | A1 * | 3/2020 | Nematihosseinabadi ................... G10L 15/02 |
| 2020/0349921 | A1 * | 11/2020 | Jansen .................... G10L 25/51 |
| 2020/0411036 | A1 * | 12/2020 | Daimo .................. G06V 40/20 |
| 2022/0059117 | A1 * | 2/2022 | Shor ....................... G10L 25/48 |
| 2022/0130415 | A1 * | 4/2022 | Garrison ............... G10L 15/063 |
| 2022/0409089 | A1 * | 12/2022 | den Brinker .......... G16H 50/20 |
| 2024/0161769 | A1 * | 5/2024 | Garrison ................ G10L 25/30 |

OTHER PUBLICATIONS

Larson et al., "Accurate and Privacy Preserving Cough Sensing using Low-Cost Microphone," UbiComp'11/Beijing, China, 2011, pp. 375-384.

Liu et al., "Cough event classification by pretrained deep neural network," BMC Medical Informatics and Decision Making, 2015, 10 pages, vol. 15, Suppl. 4.

Peplinski et al., "Frill: A Non-Semantic Speech Embedding for Mobile Devices," University of Washington et al., 2021, 5 pages.

Pham, Cuong, "MobiCough: Real-Time Cough Detection and Monitoring Using Low-Cost Mobile Devices," Asian Conference on Intelligent Information and Database Systems. ACIIDS 2016, Lecture Notes in Computer Science, 4 pages, vol. 9621.

Shor et al., "Improving Speech Representations and Personalized Models Using Self-Supervision," Google AI Blog, 2020, 6 pages.

Shor et al., "Towards Learning a Universal Non-Semantic Representation of Speech," Google Research, Israel et al., 2020, 5 pages.

Vocalis Health Products: Using Voice to get back to work, https://vocalishealth.com, 2021, 5 pages.

* cited by examiner

900

| Name | Description | Values |
|---|---|---|
| MV3Size | MobileNetV3 size | tiny, small, large |
| MV3Width | MobileNet width | 0.5, 0.75, 1.0, 1.25, 1.5, 2.0 |
| GAP | Global average pooling | yes, no |
| Compression | Bottleneck compression | yes, no |
| QAT | Quantization-aware training | yes, no |

1810 PERFORMING ONE OR MORE PRE-PROCESSING STEPS ON THE AUDIO STREAM TO GENERATE AN INPUT AUDIO SEQUENCE COMPRISING A PLURALITY OF TIME-SEPARATED AUDIO SEGMENTS

1820 GENERATING AN EMBEDDING FOR EACH OF THE SEGMENTS OF THE INPUT AUDIO SEQUENCE USING AN AUDIO FEATURE SET GENERATED BY A SELF-SUPERVISED TRIPLET LOSS EMBEDDING MODEL, THE EMBEDDING MODEL HAVING BEEN TRAINED TO LEARN THE AUDIO FEATURE SET IN A SELF-SUPERVISED TRIPLET LOSS MANNER FROM A PLURALITY OF SPEECH AUDIO CLIPS FROM A SPEECH DATASET

1830 PROVIDING THE EMBEDDING FOR EACH OF THE SEGMENTS TO A MODEL PERFORMING COUGH DETECTION INFERENCE, THE MODEL GENERATING A PROBABILITY THAT EACH OF THE SEGMENTS OF THE INPUT AUDIO SEQUENCE INCLUDES A COUGH EPISODE

1840 GENERATING COUGH METRICS FOR EACH OF THE COUGH EPISODES DETECTED IN THE INPUT AUDIO SEQUENCE

FIG. 18

1910 PERFORMING ONE OR MORE PRE-PROCESSING STEPS ON THE AUDIO STREAM TO GENERATE AN INPUT AUDIO SEQUENCE COMPRISING A PLURALITY OF TIME-SEPARATED AUDIO SEGMENTS

1920 GENERATING AN EMBEDDING FOR EACH OF THE SEGMENTS OF THE INPUT AUDIO SEQUENCE USING AN AUDIO FEATURE SET GENERATED BY A SELF-SUPERVISED TRIPLET LOSS EMBEDDING MODEL, THE EMBEDDING MODEL HAVING BEEN TRAINED TO LEARN THE AUDIO FEATURE SET IN A SELF-SUPERVISED TRIPLET LOSS MANNER FROM A PLURALITY OF SPEECH AUDIO CLIPS FROM A SPEECH DATASET

1930 PROVIDING THE EMBEDDING FOR EACH OF THE SEGMENTS TO A MODEL PERFORMING INFERENCE TO DETECT THE NON-SEMANTIC, PARALINGUISTIC EVENT, THE MODEL GENERATING A PROBABILITY THAT EACH OF THE SEGMENTS OF THE INPUT AUDIO SEQUENCE INCLUDES SUCH AN EVENT

FIG. 19

METHOD FOR DETECTING AND CLASSIFYING COUGHS OR OTHER NON-SEMANTIC SOUNDS USING AUDIO FEATURE SET LEARNED FROM SPEECH

CROSS-REFERENCE TO RELATED APPLICATIONS/INCORPORATION BY REFERENCE

This application claims priority to U.S. patent application Ser. No. 17/507,461, filed Oct. 21, 2021, which claims priority to U.S. Provisional Patent Application No. 63/104,291, filed on Oct. 22, 2020, which are hereby incorporated by reference in their entirety.

BACKGROUND

This disclosure relates to a method for detecting coughs, or other non-semantic/paralinguistic sounds such as snoring, wheezing, hiccup, or breathing through a mask, in an audio recording.

FDA (U.S. Food and Drug Administration) policy allows FDA-cleared non-invasive, vital sign-measuring devices to expand their use so that health care providers can use them to monitor patients remotely. The devices include those that measure body temperature, respiratory rate, heart rate and blood pressure. The FDA has indicated that by allowing these devices to be used remotely they can help health care providers access information about a patient's vital signs while the patient is at home, reducing the need for hospital visits and, at least at the present time, minimizing the risk of exposure to coronavirus.

The utility of cough tracking is still widely unexplored. Historically, cough tracking systems have been considered cumbersome, expensive and unreliable, and include cumbersome and/or expensive equipment such as vests, neck mics, chest straps, and tape recorders.

Recent advancements have enabled affordable, and scalable cough tracking via on-device sound detection. Regulatory groups like the FDA are eager and ready to fast track remote monitoring in this arena for several reasons. Specifically, cough acoustic properties and trends can help clinicians diagnose and treat various diseases. It is known that viruses and bacteria have learned to hijack the cough reflex in order to spread more efficiently to new hosts. Frequent coughing can indicate the presence of a disease, for example it can be caused by some sort of respiratory tract infection. Coughing can also be triggered by smoking, air pollution, asthma, allergies, acid reflux, heart failure, lung tumors or medications. Typically, treatment will target the cause, i.e. smoking cessation, inhaler etc. Cough suppressants are prescribed, but are shown to have little effect. Coughing is a natural protective reflex, in some cases suppressing the cough reflex can be damaging, especially if the cough is productive. Treatment often involves patient self-reporting, however self-reporting of cough frequency and severity is notoriously unreliable.

Additionally, coughs can be classified or characterized in different ways. A dry cough is the most common for colds, allergies, and asthma, whereas a wet cough is considered productive as it brings up phlegm from the lower respiratory tract helping to remove fluid from the lungs. Knowing if a cough is dry or wet helps identify the cause, severity and treatment of the underlying medical condition. This wet/dry distinction can often be made from the sound qualities of the cough.

There are several common clinical questions that pertain to coughing episodes, such as: How long has the cough lasted? Days, weeks, months? When is the cough most intense? Night, morning, intermittently throughout the day? How does the cough sound? Dry, wet, barking, hacking, loud, soft? Does the cough produce other symptoms? Such as vomiting, dizziness, sleeplessness or something else? How bad is your cough? Does it interfere with daily activities, is it debilitating, annoying, persistent, intermittent?

This disclosure meets a need for a method for identifying a cough in an audio stream and generating metrics about cough episodes automatically. These metrics can then be used to assist a health care provider is answering these clinical questions and thereby improving patient care. The method can be implemented in computer devices equipped with a microphone for recording sounds and a processor implementing the methods described in this document for example smart home virtual assistant and automation devices, portable computers such as laptops, smartphones and table computers, and the like.

SUMMARY

As described herein, an audio feature set derived from speech samples can be used to detect cough episodes or other non-semantic, paralinguistic sounds in an audio stream. Also described herein is a method of using the audio feature set in a cough detection model that can be embodied in a smartphone or other computer device and thereby be used to collect de-identified cough data and generate metrics relating to cough episodes. Such metrics can be used to classify or characterize the cough episodes using models built on top of a cough detection model.

The audio feature set (or representation) can be described as a multidimensional vector or embedding of numbers or values, e.g., a 512 or 1024 dimensional vector. This vector or embedding is learned in a self-supervised manner on speech containing audio clips. This representation is referred to as TRILL embeddings below (TRILL being an acronym of TRipLet Loss network). One example of a collection of speech samples used to generate this representation is known as "AudioSet," a large and diverse dataset that includes 2500 hours of speech. However, other datasets of speech samples could be used instead. This audio feature set may be learned in a self-supervised manner from the AudioSet speech clips.

In one embodiment, a computer-implemented method for detecting a cough in an audio stream includes the following steps: performing one or more pre-processing steps on the audio stream to generate an input audio sequence comprising a plurality of time-separated audio segments; generating an embedding for each of the segments of the input audio sequence using an audio feature set generated by a self-supervised triplet loss embedding model, the embedding model having been trained to learn the audio feature set in a self-supervised triplet loss manner from a plurality of speech audio clips from a speech dataset; providing the embedding for each of the segments to a model performing cough detection inference, the model generating a probability that each of the segments of the input audio sequence includes a cough episode; and generating cough metrics for each of the cough episodes detected in the input audio sequence.

In another embodiment, a computing device for detecting a cough in an audio stream is provided. The computing device includes one or more processors operable to perform operations. The operations include: performing one or more pre-processing steps on the audio stream to generate an input audio sequence comprising a plurality of time-separated audio segments for a machine learning model; generating an embedding for each of the segments of the input audio sequence using an audio feature set generated by a self-supervised triplet loss embedding model, the embedding model having been trained to learn the audio feature set in a self-supervised triplet loss manner from a plurality of speech audio clips from a speech dataset; implementing a model performing cough detection inference on the embedding generated by code b), wherein the model generates a probability that each of the segments of the input audio sequence includes a cough episode; and generating cough metrics for each of the cough episodes detected in the input audio sequence.

In another embodiment, a computer-implemented method for detecting a non-semantic, paralinguistic event in an audio stream is provided. The computing device includes one or more processors operable to perform operations. The operations include: performing one or more pre-processing steps on the audio stream to generate an input audio sequence comprising a plurality of time-separated audio segments; generating an embedding for each of the segments of the input audio sequence using an audio feature set generated by a self-supervised triplet loss embedding model, the embedding model having been trained to learn the audio feature set in a self-supervised triplet loss manner from a plurality of speech audio clips from a speech dataset; and providing the embedding for each of the segments to a model performing inference to detect the non-semantic, paralinguistic event, the model generating a probability that each of the segments of the input audio sequence includes such an event.

This disclosure further demonstrates that the audio feature set can be used in specific machine learning models to detect coughs, and have the potential to be used simultaneously for other tasks like cough identification, and cough-type classification. The technique is small and fast enough to be used on a device like a smartphone, and can also be used to collect patient de-identified cough data. This technique has similar or improved performance, while offering improved latency performance and significantly improved privacy properties.

In one embodiment of implementation of the method, there is an initial calibration or "enrollment" process in which a user is instructed to generate an audio stream in order to conduct a calibration procedure. In this "enrollment" audio stream, the user is instructed to cough n times, with n typically between 5 and 10, and the coughs are recorded, e.g., in the smartphone using the audio recording app. An embedding for each detected cough is generated using the audio feature set. A similarity metric or, equivalently, distance is determined between each pairwise combination of the n coughs. A verification threshold is then computed. This verification threshold is used by the model performing cough detection inference; the verification threshold is based on the computed distances. Later, after the enrollment process is completed, when a new cough is detected in an audio stream, the distance is measured between the newly detected embedding (vector) and all of the n enrollment cough embeddings, and the median distance, e.g., Euclidean distance or "inferred cough distance" is computed which reflects the distance between the user's enrollment coughs and the newly inferred, unverified cough. If this inferred cough distance is less than the verification threshold, then it is determined that the cough originated from the user, otherwise it is assumed that the cough originated from another, unverified source (e.g., a different person in the room where the audio recording was made). If the cough originated from another unverified source the cough statistics, characterization or identification steps may be disregarded, for example.

BRIEF DESCRIPTION OF THE FIGURES

FIG. 9 illustrates example values of a width multiplier, in accordance with example embodiments.

FIG. 18 is a flowchart of a method, in accordance with example embodiments.

FIG. 19 is another flowchart of a method, in accordance with example embodiments.

DETAILED DESCRIPTION

Figure 1:
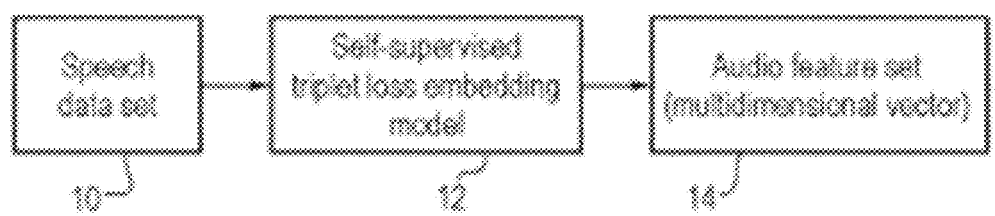
FIG. 1 is an illustration of a method of obtaining an audio feature set from a speech data set which is then used for cough detection.

As noted above, our method for cough detection makes use of an audio feature set (or representation) can be described as a multidimensional vector or embedding, e.g., a 512 or 1024 dimensional vector, which in some sense represents non-semantic, paralinguistic representation of speech. FIG. 1 shows the manner in which this feature set is obtained. In particular, a speech data set consisting of a plurality of speech audio clips is obtained, for example the AudioSet mentioned previously. A self-supervised triplet loss model 12 may be trained in a self-supervised manner on this speech set and configured to generate an audio feature set 14 (multidimensional vector, e.g., vector of dimension 512 or 1024), which is a general representation of non-semantic, paralinguistic speech.

As noted above, one possible example of this collection of speech samples 10 is known as AudioSet. Additional, and/or alternative sets of speech samples may be used, and could include tens of thousands or more speech samples from a plurality of people of different ages and speaking different languages, or all the same language, e.g., English.

Figure 2:
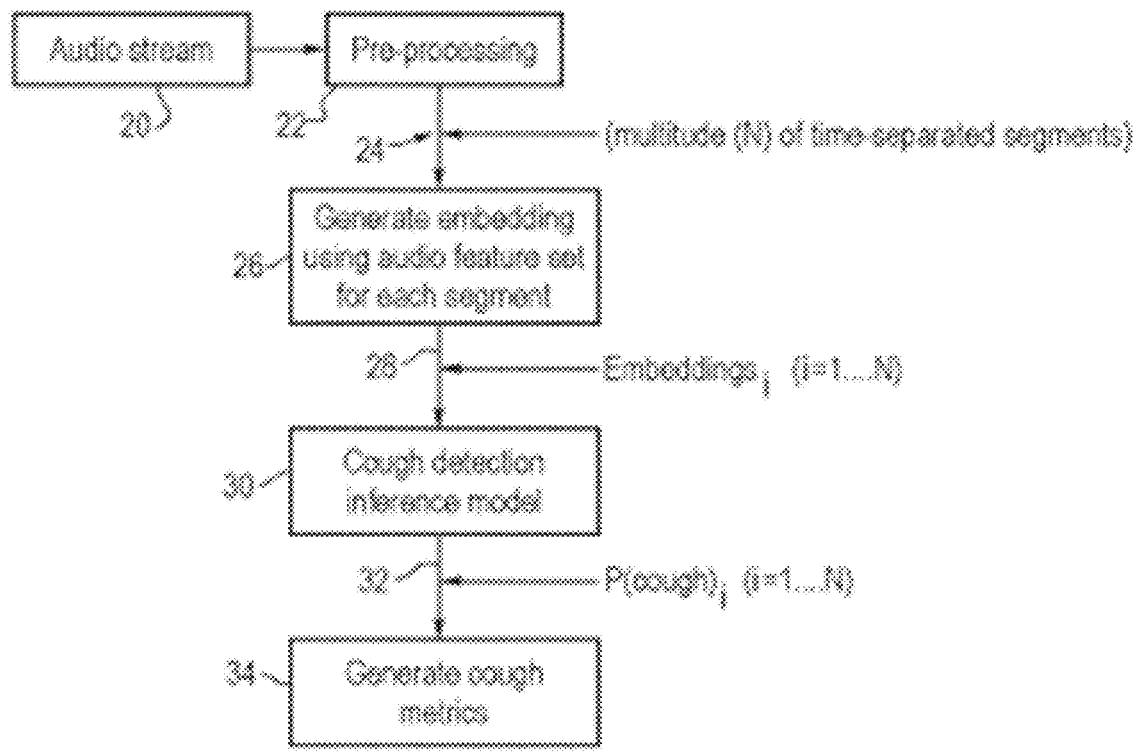
FIG. 2 is a flow chart showing a method for detecting a cough in an audio stream using the audio feature set obtained from FIG. 1.
Figure 6:
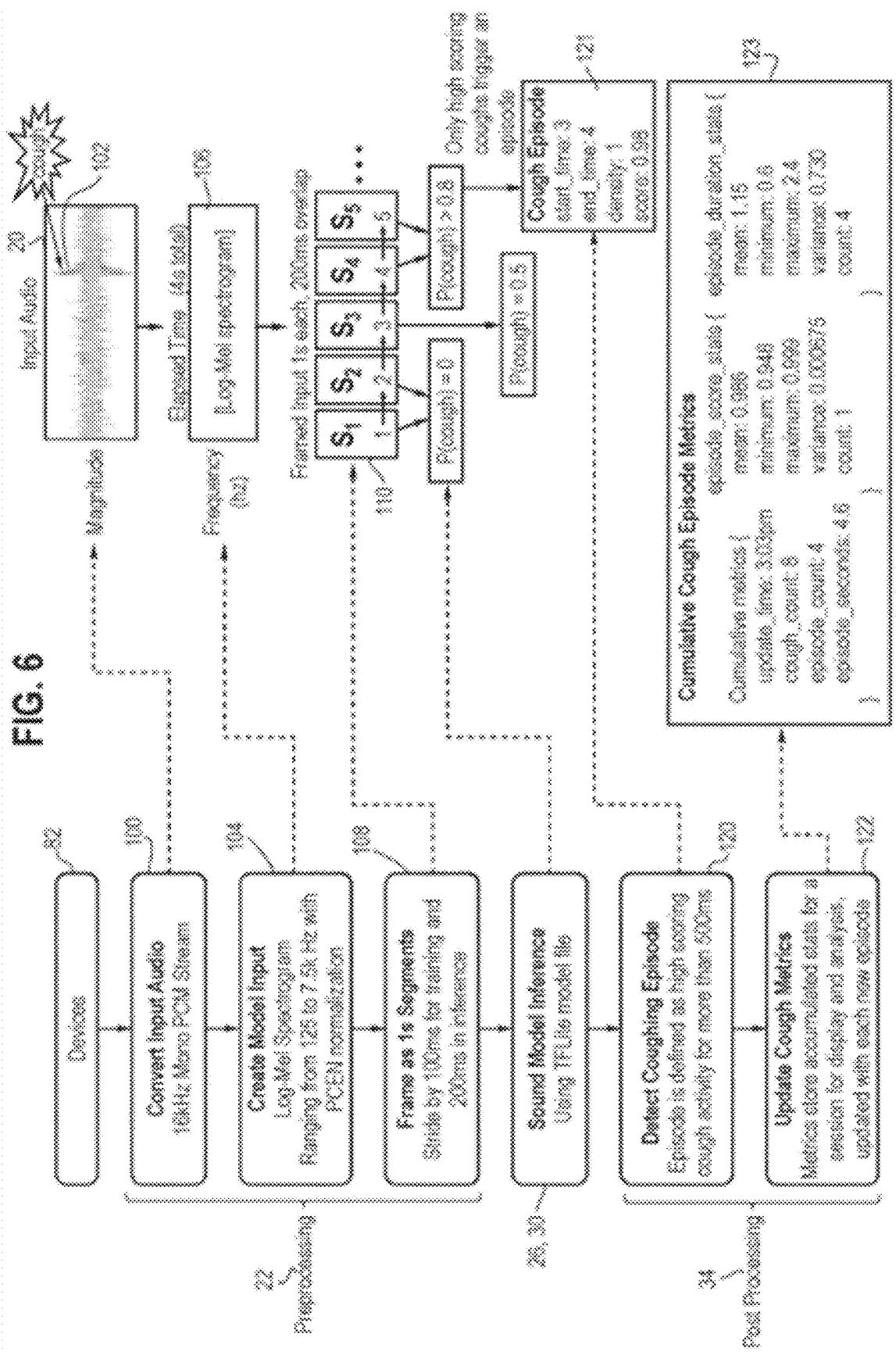
FIG. 6 is a more detailed illustration of another embodiment of the process of FIG. 2.
Figure 7:
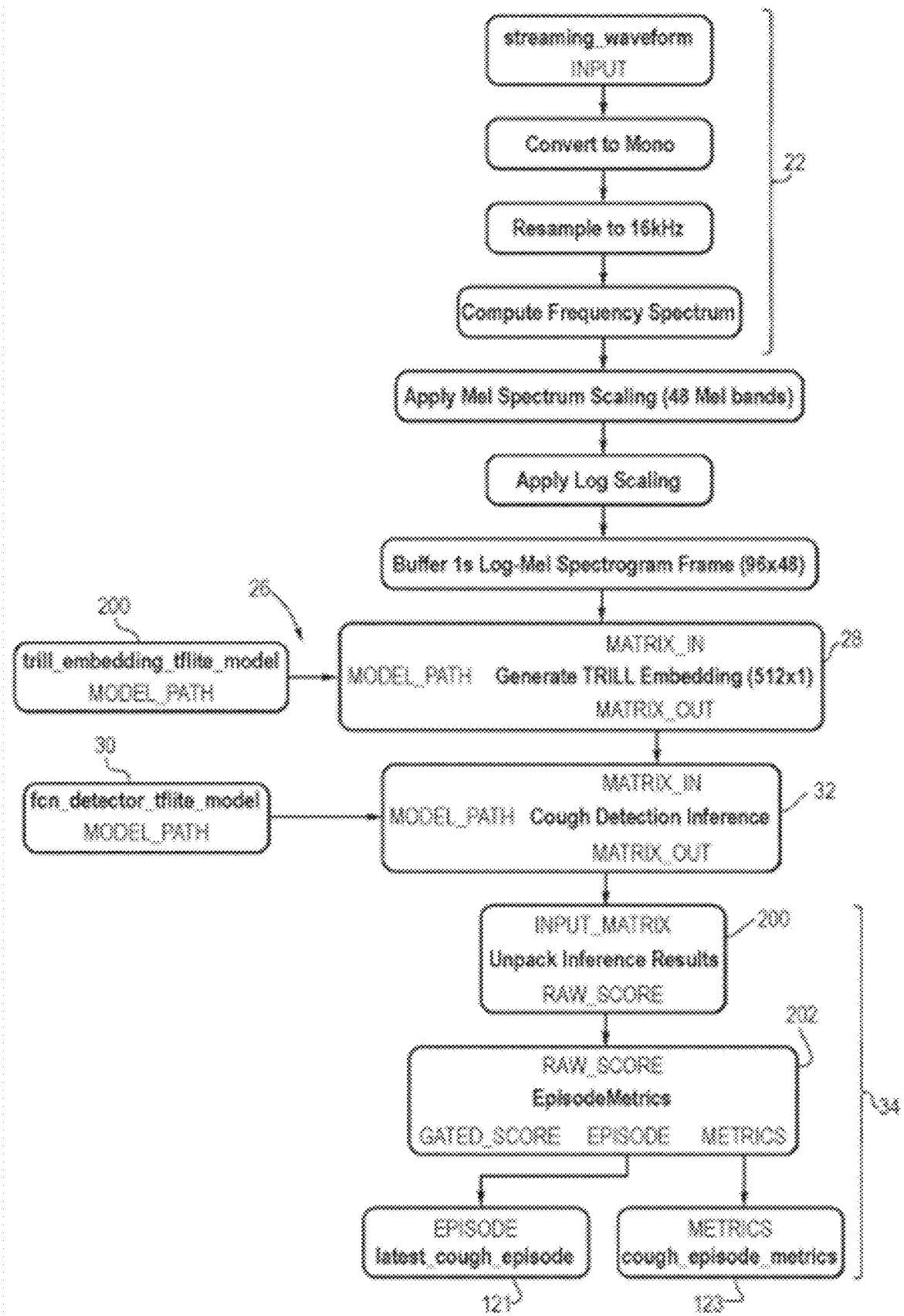
FIG. 7 is another more detailed illustration of another embodiment of the process of FIG. 2.

Once the feature set 14 is obtained as per FIG. 1, it is then used in a cough detection process or methodology which is outlined in FIG. 2. FIGS. 6 and 7 provide more details on specific embodiments of the methodology of FIG. 2.

Referring to FIG. 2, our method provides for detecting a cough in an audio stream 20. This audio stream 20 will typically be in the form of a digital sound recording, e.g., captured by the microphone of a device such as a smartphone, or intelligent home assistant, personal computer, etc. This audio stream is provided to a computer system which includes executable code stored in memory that performs certain processing steps, indicated at blocks 22, 26, 30 and 34.

In particular, at block 22 there is a pre-processing step performed. Basically, this step converts the audio stream 20 into an input audio sequence in the form of a plurality of time-separated audio segments, e.g., segments of 1 second duration, possibly with some overlap between the segments. The pre-processing step can include sub-steps such as computing a frequency spectrum for the audio segments, providing Mel-spectrum scaling or conversion to Mel-spectrographs (described below) or other steps depending on the implementation. The result of the pre-processing step is the plurality of time separated segments 24, e.g., N such segments, with the value of N being dependent on the length or duration of the audio stream. N can vary from 1 to a thousand, 10,000 or even more, for example where the duration of the audio stream is on the order of hours or even days.

At step 26, there is a step of generating an embedding for each of the segments of the input audio sequence using the audio feature set learned in a self-supervised triplet loss manner from a plurality of speech audio clips from a speech dataset (i.e., the feature set 14 of FIG. 1). The manner of generating this embedding is described in FIGS. 6 and 7 and described in more detail below. Generally speaking, a TRILL embedding model is applied to input segments and the result is a matrix of embeddings 28 1 . . . N, e.g., each of dimension 512 or 1024, where N is the number of time-separated audio segments as explained above.

Non-semantic aspects of the speech signal (e.g., speaker identity, language, and emotional state) generally change more slowly than the phonetic and lexical aspects that are used to convey meaning. Therefore, a good representation may be expected for non-semantic downstream tasks to be considerably more stable in time. To take advantage of this intuition, temporal proximity may be utilized as a self-supervision signal.

More formally, consider a large, unlabeled speech collection represented as a sequence of spectrogram context windows $X=x_1, x_2, \ldots, x_N$, where each $x_i \in \mathbb{R}^{F \times T}$. A map g may be learned, $g: \mathbb{R}^{F \times T} \to \mathbb{R}^d$ from spectrogram context windows to d-dimensional space such that $\|g(x_i)-g(x_j)\| \leq \|g(x_i)-g(x_k)\|$ when $|i-j| \leq |i-k|$. Such a relationship may be expressed as a learning objective using triplet loss based metric learning as follows. First, a large collection of example triplets of the form $z=(x_i, x_j, x_k)$ (the so-called anchor, positive, and negative examples), may be sampled from X, where $|i-j| \leq \tau$ and $|i-k| > \tau$ for some suitably chosen time scale $\tau$. The loss incurred by each triplet may be determined as:

$$\mathcal{L}(z) = \sum_{i=1}^{N} \left[ \|g(x_i) - g(x_j)\|_2^2 - \|g(x_i) - g(x_k)\|_2^2 + \delta \right]_+ \quad \text{(Eqn. 1)}$$

where $\|\cdot\|_2^2$ is the $L_2$ norm, $[\cdot]_+$ is a standard hinge loss, and $\delta$ is a nonnegative margin hyperparameter. The standard within-batch, semi-hard negative mining technique may be applied.

The TRILL model may be trained on the subset of AudioSet training set clips possessing the speech label. The time scale $\tau$ may be set to 10 seconds, the maximum duration of each AudioSet clip. This can make the training task a primarily same clip/different clip discrimination. Also, for example, (i) log Mel spectrogram context windows with F=64 Mel bands and T=96 frames representing 0.96 seconds of input audio (STFT computed with 25 ms windows with step 10 ms) may be taken as input; and (ii) a variant of the standard ResNet-50 architecture followed by a d=512 dimensional embedding layer may be employed. Since the ResNet's final average pooling operation may destroy the sub second temporal structure, representations defined by earlier convolutional blocks may be additionally considered.

Once these embeddings 28 are obtained they are supplied to a cough detection inference model (e.g., fully connected layers of a neural network trained to recognize coughs) which then generates a probability Pi (cough) for each of the i=1 . . . N audio segments, indicated at 32. At step 34, these cough probabilities, along with other information, are used to generate cough metrics for the N audio segments which describe things such as the duration of a cough episode, type of cough, characterization of the cough. The cough metrics can consist of metrics for each particular cough that was detected, as well as metrics for cough episodes, e.g., discrete time periods where a person is coughing at some minimum rate.

In one embodiment of implementation of the method, the method of detecting coughs of FIG. 2 takes into consideration the possibility that it is desirable to only analyze coughs of a particular individual, and thus be able to detect that a cough came from a particular individual (e.g., referred to as the "user" here), for example where the audio stream is in recording sounds in an environment in which there is more than one person present and the purpose of the cough detection is to detect coughs (and perhaps classify or characterize the coughs) of a particular person, here the user, and disregard other coughs or coughing sounds from other persons who may happen to be present while the recording is made.

Figure 3:
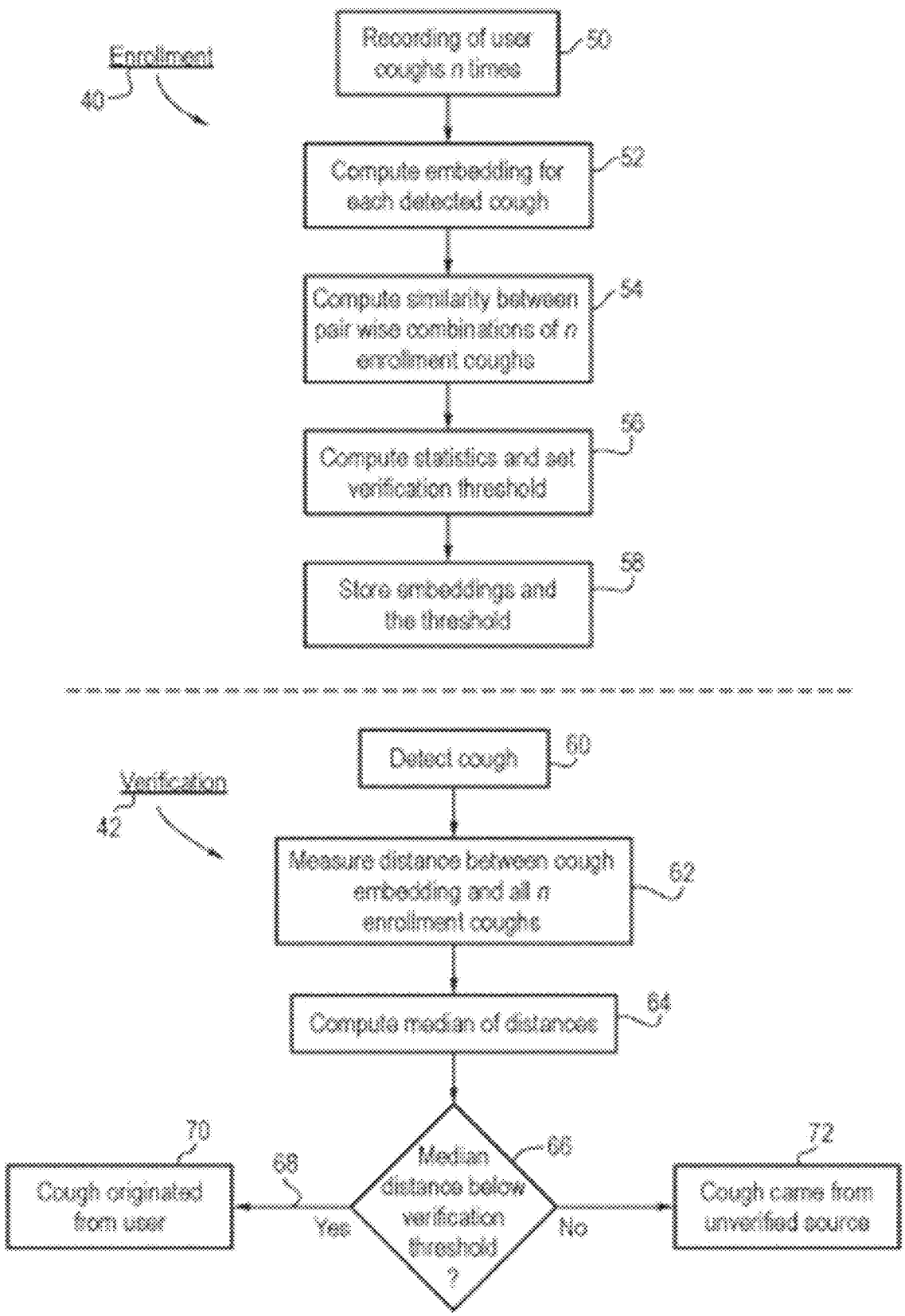
FIG. 3 is a flowchart of enrollment and verification processes; such processes can be used in conjunction with the methodology of FIG. 2.

A cough identification enrollment 40 and verification 42 process shown in FIG. 3 is used in this situation. The verification process 42 assumes that there is a known user that has been enrolled in some form of procedural calibration where they are instructed to cough a few times. The enrollment process 40 results in an "anchor" TRILL embedding cluster which serves as the basis for determining whether future coughs originated from the user or some other source.

The theory behind the procedure of FIG. 3 works due to the assumption that coughs from the same person sound more similar than coughs from different people. Since TRILL embeddings summarize sound properties, it is also assumed that TRILL cough embeddings from the same person are more similar to each other than TRILL cough embeddings from different people. The similarity metric section below summarizes how the similarity of two embeddings can be measured.

Much of the acoustic properties of a cough are specific to an individual's unique vocal chords. In fact, prior research shows that the last ~100 ms of a cough, often called the 'voiced region' is unique to an individual while the 'explosive region' at the cough onset is less unique to a person.

Figure 8A:
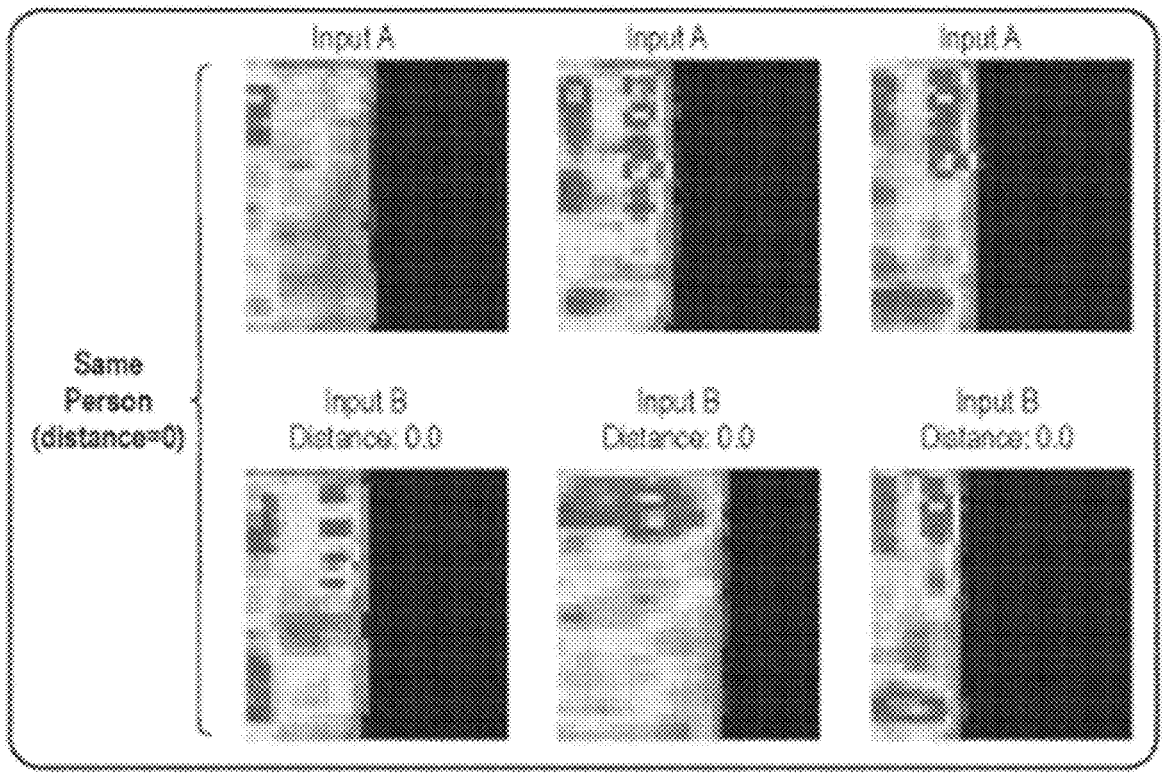
FIG. 8A is a plot of Mel-spectrograms for a series of coughs from the same person.
Figure 8B:
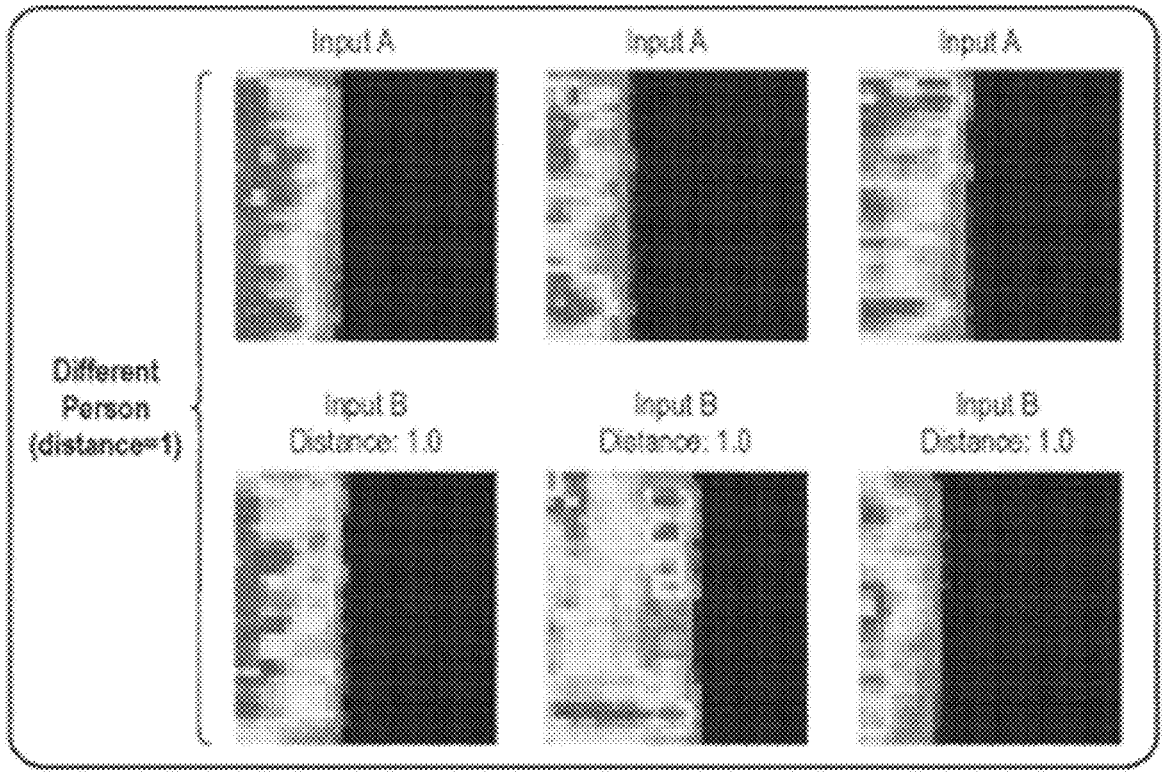
FIG. 8B is a plot of Mel-spectrograms for a series of coughs from different persons.

While the procedure of FIG. 3 describes performing cough-id verification using TRILL embeddings, the task can be done fairly intuitively by simply looking at side-by-side audio spectrograms of a cough from the same person (FIG. 8A) and different people (FIG. 8B). In these spectrograms, the x axis represents time and they axis represents frequency (from low to high). The spectrograms of FIGS. 8A and 8B are known as "Mel spectrograms", which are known methods in signal and acoustic processing for representing a sound signal. To create such spectrograms, a digitally represented audio signal is mapped from the time domain to the frequency domain using the fast Fourier transform; this is performed on overlapping windowed segments of the audio signal. The y-axis (frequency) is converted to a log scale and the color dimension (amplitude) to decibels to form the spectrogram. The y-axis (frequency) is mapped onto the Mel scale to form the Mel spectrogram. The Mel scale is a perceptual scale of pitches judged by listeners to be equal in distance from one another. The reference point between this scale and normal frequency measurement is defined by assigning a perceptual pitch of 1000 Mels to a 1000 Hz tone, 40 dB above the listener's threshold. Above about 500 Hz, increasingly large intervals are judged by listeners to produce equal pitch increments. As a result, four octaves on the hertz scale above 500 Hz are judged to comprise about two octaves on the Mel scale.

The voiced region of the cough is not always visible, but when it is it shows as a stack of horizontal 'bars' in the upper frequencies near the cough offset. Because this region is based on vocal cord resonance properties it is typically the case that this pattern is similar for all of an individual's coughs regardless of the volume or duration or cause of the cough.

As mentioned above, the procedure of FIG. 3 includes an enrollment process 40 and a verification process 42. The initial calibration or "enrollment" process 40 includes a step in which the user is instructed to generate an audio stream 50 in order to conduct a calibration procedure. In this "enrollment" audio stream 50, the user is instructed to cough n times, and the coughs are recorded, e.g., in the smartphone using the audio recording app. n is typically a value between 5 and 10. At step 52 a TRILL embedding for each detected cough is generated using the audio feature set (see step 26 of FIGS. 2 and 7). At step 54 a similarity or distance is determined between each pairwise combination of the n coughs. This results in "n choose 2" distances where K=2, we call this set the intra-enrollment distances.

Figure 4:
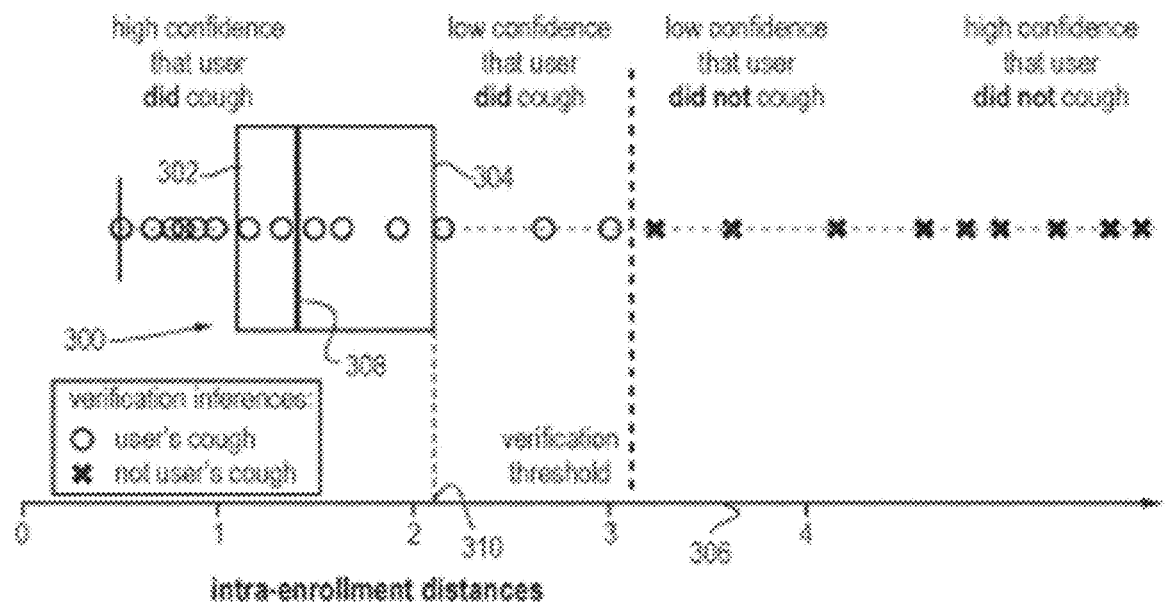
FIG. 4 is a plot of distances and a verification threshold for a series of coughs, showing both the plot of distances for enrollment coughs indicated by the box as well as distances for coughs that fall above and below the verification threshold.

At step 56 standard statistics are computed from the intra-enrollment distances which may look like the box-whisker plot 300 shown in FIG. 4, where the boundaries 302, 304 of the box along the axis 306 represent the range of distances which are computed and the solid line 308 represents some average or median of the distances. Since intra-enrollment distances are all from the same person it is assumed that the distances between them is relatively low as they should sound similar, the embeddings for each cough do not different substantially from each other, and therefore the intra-cough distances are relatively low. Also at step 45 a verification threshold is automatically chosen based on the intra-enrollment distance. The logic for choosing the threshold can vary, but for simplicity, this threshold may be generally chosen to be the right (greater than) highest value of the intra-enrollment distance in box-whisker plot, 310. In the example of FIG. 4 it would be set at say 3.1.

At step 58 the n enrollment TRILL embeddings are stored for future reference as well as the automatically selected verification threshold.

The verification process 42 requires enrollment (procedure 40) to have been completed and is triggered whenever a cough is detected in an audio stream, step 60. At step 62, the distance is measured between the newly detected cough TRILL embedding (vector) and all of the n enrollment cough embeddings, resulting in n distances. At step 64 the median distance from this set is selected (or computed) which represents the distance between the user's enrollment coughs and the newly inferred, unverified cough. At step 66 a test is performed: if this inferred cough distance is less than the verification threshold (computed in the enrollment process 40 at step 56), branch 68 is taken and at step 70 it is determined that the cough originated from the user, otherwise at step 72 it is determined that the cough originated from another, unverified source (e.g., a different person in the room where the audio recording was made). If the cough originated from another unverified source the cough statistics, characterization or identification steps may be disregarded, for example.

The verification threshold allows the verification to be binary (either the cough is from the user or not). The confidence in the classification can be determined from the magnitude of the inferred cough distance. As the inferred cough distance approaches 0, the classification increases in confidence. Conversely as the inferred cough distance approaches infinity, the confidence approaches 0.

We recognize there are several potential issues with the procedure of FIG. 3. It is possible for a user's cough acoustics to change over time, perhaps due to an illness, aging, or a change in the room acoustics. This means that enrollment procedure 40 of FIG. 3 will likely need to happen periodically or re-trigger if inferred coughs are nearly always exceeding the verification threshold. There are many ways an app (e.g., one resident on a smartphone which is used for the cough detection method) could determine if enrollment needs to be redone, some smarter than others. For example, there could be a pop-up that is shown when a cough is detected (some probability of the time) asking the user: "did you just cough?". If the user's answer disagrees with the cough-id verification algorithm some number of times, the enrollment could be retriggered.

A significant component to the procedure of FIG. 3 is the task of measuring the similarity between two TRILL cough embeddings, which we have called the "distance" in this discussion. Since the embeddings are fixed in length (e.g. 512), standard vector norm mathematics can be used (i.e., $L_2$, $L_1$, $L_\infty$, etc.). The most straightforward metric, $L_2$ or Euclidean Distance, is used and defined below (where p and q are TRILL embedding vectors with length n).

Learned Similarity Metric $L_2$ distance gives equal weight to the n entries in the embedding, however it may be the case that some subset of the indices in the TRILL embedding are especially useful for the cough-id task, while others may be better suited for perhaps the cough detection task. If this were the case, a weighted distance metric which associates higher weight to the TRILL embedding indices that are useful for the tasks would be ideal. This weighted distance metric could be learned from some cough-id dataset to best minimize the distance between same coughs and maximize the distance between different coughs and would likely make it easier to choose an optimal verification threshold.

Figure 5:
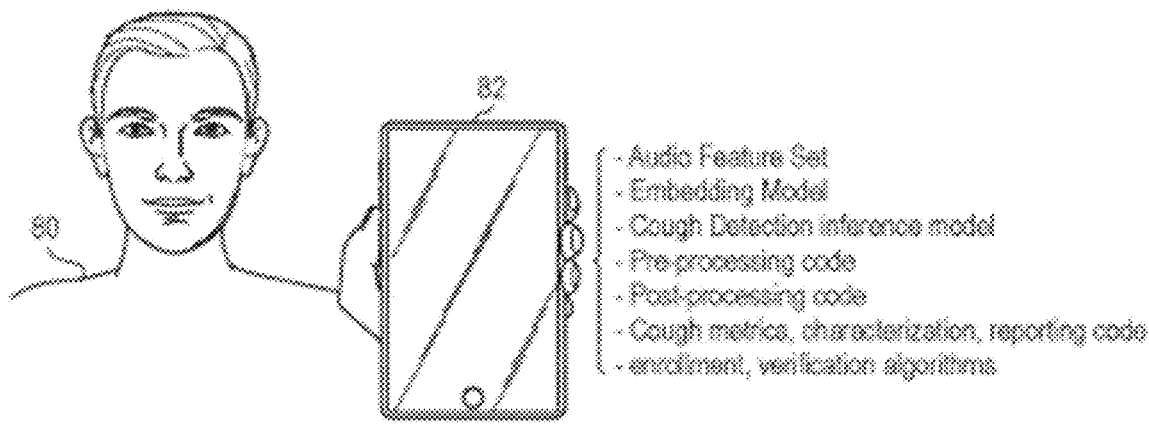
FIG. 5 is an illustration of a computing device, in the form of a smartphone, which can be used as a device for detecting and classifying a cough of a user.

FIG. 5 illustrates one possible environment in which the present disclosure is practiced. The user 80 has a smartphone 82 (or tablet, laptop, or other computing machine equipped with a microphone and processing unit) which serves to record sounds and generate an audio stream used in the methods of FIGS. 2 and 3. The smartphone includes the audio feature set of FIG. 1, an embedding model for generating embeddings based on coughs detected from the user 80, a cough detection inference model, pre-processing code, post-processing code, e.g., generating cough metrics, cough episode metrics, and characterization of the coughs or cough episodes, and code for reporting the cough or cough metrics e.g. to the user, to a primary care physician, or to some external entity, while preserving patient privacy, confidentiality and in accordance with all applicable standards, e.g., HIPAA. The code resident on the smartphone 82 can optionally include the code implementing the enrollment and verification procedures of FIG. 3, including prompts for the user.

Example 1

FIG. 6 is a flow chart showing an example of the implementation of the method of FIG. 2. A device 82 records an audio stream; the device can take the form of any piece of equipment or computer which includes a microphone and generates a recording, such as a smartphone, intelligent home assistant, etc. The audio stream is subject to pre-processing steps 22 which include sub-steps 100, 104 and 106. At step 100 the audio stream is converted to 16 kHz mono PCM stream, which is shown in box 20 including a signal 102 indicative of a cough. At step 104, create model input, a log-Mel spectrogram is created (106), ranging from 125 to 7.5 kHz with PCEN (per-channel energy normalization). This log-Mel spectrogram 106 is similar to the spectrograms shown in FIG. 8 and described previously.

At step 108, this spectrogram 106 is framed as 1 second segments, with 200 ms overlap, represented as spectra S1, S2, S3 . . . (110).

As step 26 an embedding is created for each of the segments using the audio features set from FIG. 1 (see the description of FIG. 7 below) and the embedding subject to cough detection model inference using a TFLite model file. This model produces probabilities of a cough occurring in each segment, shown as P(cough)=0 for spectra S1 and S2, P (cough)=0.5 for spectrum S3, etc. as shown in FIG. 6.

One or more post-processing steps shown at 34 are performed including detecting cough episodes at step 120 and updating or generating cough metrics 122. An example of a cough episode metric is shown at 121 and includes start and end times, density: 1 (density is the number of coughs detected in a 1 second audio segment) and score: 0.98; here the "score" is the probability produced by the cough inference model. A cough episode is defined as high scoring cough activity for more than 500 ms. An example of the cumulative cough metrics is shown at 123, such as metrics which store accumulated statistics for a session for display and analysis, updated with each new cough episode that is detected.

FIG. 7 is another example of the processing operations that perform the method of FIG. 2. The initial pre-processing steps 22 are basically the pre-processing steps 22 of FIG. 6 but broken down into individual, discrete modules. Step 26 is the step of generating the embedding for the audio segments (in the form of log-Mel spectrogram frames) and basically consists of the step of applying a TRILL embedding model "trill_embedding_tflite_model" to the log-Mel spectrogram frame to generate a TRILL embedding, in this case a vector of numbers of dimension 512×1. TFlite is a tool packaged with Tensorflow that optimizes a model (typically a neural network) for on-device inference. The conversion process from a tensorflow model file—>TFlite model file typically involves optimizing the neural network operations for the hardware of interest (for example a smartphone CPU, or an embedded DSP, or a server GPU). The conversion also allows the user to apply other various tricks to speed up the inference time, or reduce the amount of power needed (often at the cost of some model accuracy). The resulting TFLite model is typically a much smaller file size (a few megabytes) and suitable for packaging within an app that is resident on a portable computer, e.g., smart phone. In this example, the trill_embedding_tflite_model can be similar to MobileNet in some aspects, and may be configured as a sequence of convolution layers in a convolutional neural network.

Once this embedding is created, a cough detection inference model 30 may be applied to the embeddings 28 and the output is the generation of a cough detection inference matrix 32 of probabilities of a cough (P cough) for each of the audio segments. The cough detection inference model 30 in this example is a neural network trained to identify coughs, indicated at "fcn_detector_tflite_model". In some embodiments, it may include 4 fully connected 'dense' layers where each layer is half the length of the previous layer, and the final output is the cough 'score' or probability that coughing is happening.

fcn_detector_tflite_model
Input: size=512 (TRILL embedding size)
Layer 1: size=256
Layer 2: size=128
Layer 3: size=64
Layer 4: size=32
Output: size=1 (probability of coughing between 0 and 1)
The number of layers and layer sizes may vary.

The post-processing steps 34 are shown in FIG. 7 as consisting of sub-step 200 (unpack inference results), 202 (generate cough episode metrics) which consists of metrics for the latest cough episode (121) and metrics for all of the cough episodes (123). Examples of these metrics are shown in FIG. 5. Examples of such metrics include the number of cough episodes per audio segment, b) number of cough episodes in the input audio stream data sequence; c) duration of the cough episode(s) per segment; and d) duration of the cough episode(s) in the input audio stream data sequence.

The metrics which are computed in the post-processing could include performing a cough-type classification of one or more cough episodes that is detected. Such classification could be, for example, wet cough, dry cough, or cough associated with a particular type of medical condition, e.g., respiratory tract infection, emphysema, etc. Such classifications could be done with the aid of the cough inference detection model or alternatively a second neural network which is trained to characterize or distinguish between wet and dry coughs, coughs associated with particular medical conditions, etc.

Example 2

The method described above in Example 1 is used on an audio stream recorded by a smartphone. A user initiates the recording via an app resident on the phone, and the app includes an instruction set that prompts the user to go through the enrollment process of FIG. 3. After the enrollment, the user initiates the recording and goes about their daily business (or, if at night, goes to bed). The user maintains their phone on with the recording proceeding for say 4 or 8 hours. The app includes a feature to turn off the recording. The methodology of FIGS. 2, 6 and 7 proceeds during the background while the recording is made, or, alternatively is initiated at the end of the recording. After the app generates all the cough metrics (step 34, FIG. 2) the user is prompted with a message such as: "Where would you like to have the cough metrics sent?" The user is provided with an option to select their primary care provider, and the audio stream portions that recorded coughs, along with the cough metrics, are sent via a secure link to an electronic medical records system maintained by the primary care provider, where the cough metrics and the actual sound segments of the coughs are available to the provider to help provide care for the patient, while preserving privacy and confidentiality of the information sent to the provider.

Example 3

A user has an intelligent home assistant, which includes speech recognition capability, and a speaker that allows the assistant to converse with the user. The following dialog between the user and the assistant proceeds along the following lines:

User: "Assistant, I would like to make a recording of my coughs for my doctor."

Assistant: "OK. First, we need to go through an enrollment process. Please cough 5 times."

User: [Coughs 5 times; Assistant records sounds of coughs and performs the enrollment process of FIG. 3].

Assistant: "Thank you. I have now completed the enrollment process. I am ready to start the recording. When would you like to start it and how long do you want me to record?"

User: "Start Now. Please record my sounds for the next 5 hours."

Assistant: "OK. I am recording your sounds and will stop recording after 5 hours. What would you like me to do with the recording and cough metrics that I generate based on the recording?"

User: "Please connect to the ["System X", an electronic medical records system used by the user's primary care provider] and upload the recording and cough metrics for my Doctor, Bob Carlson."

Assistant. "OK." [Recording by the Assistant starts.]

The user proceeds to go about their business and the Assistant records sounds for the next 5 hours. The cough verification process of FIG. 3 identifies those sounds which are coughs of the user and ignores all other sounds, including coughs of other persons (such as the user's domestic partner or children). Either during or immediately after the end of the recording the Assistant generates the cough metrics, establishes a secure link to the "System X" and the pathway to the electronic medical records for the User (or to a server that maintains such records), and uploads the portions of the audio stream that contain cough episodes as well as all the cough metrics which were calculated.

Other Possible Non-Semantic, Paralinguistic Uses

The methods of this disclosure can also be used to detect and characterize other types of non-speech vocal sounds, such snoring, wheezing, determining whether the speaker is wearing a mask or not, and still others. The methodology for detecting or characterizing these other non-speech vocal sounds is basically the same as described above for coughs, and uses the same TRILL audio feature set obtained per FIG. 1. Instead of a cough detection inference model, the method uses a model trained to recognize the specific non-semantic/paralinguistic sound for this application, such as snoring or wheezing for example.

The TRILL audio feature set used in the cough detection work of this document is a general-purpose representation of non-semantic speech. A linear model on the TRILL representation appears to outperform the best baseline model, which is a fusion of many models, despite TRILL being trained only on a completely different dataset. Fine tuning the TRILL model on mask data appears to improve accuracy by 3.6% on the Unweighted Average Recall score.

Further to the descriptions above, a user may be provided with controls allowing the user to make an election as to both if and when systems, programs, or features described herein may enable collection of user information (a user's preferences, health information, recordings or statistics/metrics of cough or other non-semantic data, or a user's current location). In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

Fast TRILL (FRILL)

Learned speech representations can improve performance on tasks with limited labeled data. However, due to their size and complexity, learned representations have limited utility in mobile settings where run-time performance can be a significant bottleneck. A class of lightweight non-semantic speech embedding models may be utilized in such situations, that run efficiently on mobile devices based on the TRILL speech embedding. Novel architectural modifications may be combined with existing speed-up techniques to create embedding models that are fast enough to run in real-time on a mobile device, and that exhibit minimal performance degradation on a benchmark of non-semantic speech tasks. For example, FRILL can be 32× faster on a Pixel 1 smartphone and yet comprise 40% the size of TRILL, with an average decrease in accuracy of only 2%. FRILL is a non-semantic embedding of a high quality that is designed for use on mobile devices. The representations described as part of FRILL can be useful for mobile health tasks such as, for example, detection of non-speech human sounds, and detection of face-masked speech.

Many of the tasks in the non-semantic speech (NOSS) benchmark, such as keyword detection and speaker identification, have natural mobile computing applications (e.g. verifying a user and triggering a voice assistant). On a mobile device, a non-semantic speech embedding could be used as input features for several real-time audio detection tasks, considerably reducing the cost of running models simultaneously. Such an embedding could enable mobile devices to listen for additional events such as non-speech health sounds (e.g. coughing, sneezing) with minimal impact on battery performance. This is desirable as real-time analysis of mobile audio streams has shown to be useful for tracking respiratory symptoms.

However, TRILL is based on a modified version of ResNet50, which is expensive to compute on mobile devices. Accordingly, in some aspects, TRILL may be distilled to a student model including a truncated MobileNet architecture, and two large dense layers (TRILL-Distilled). TRILL-Distilled can exhibit minimal performance degradation on most NOSS tasks. Due to the size of its final dense layers, TRILL-Distilled may contain over 26 M parameters, which may still be too large to run in real-time on many devices.

This performance gap may be addressed by creating non-semantic speech embeddings that are fast and small enough to run in real-time on mobile devices. To do this, knowledge distillation can be used to train efficient student models based on MobileNetV3 to mimic the TRILL representation. A combination of novel architectural modifications and existing speed-up techniques such as low-rank matrix approximation, and weight quantization may be applied to further optimize student embeddings. Finally, in addition to the NOSS benchmark, a quality of these embeddings on two privacy-sensitive, health-sensing tasks: human sounds classification and face-mask speech detection may be evaluated.

Accordingly, in some aspects, (i) a class of non-semantic embedding models may be generated that are fast enough to run in real-time on a mobile device. One example model, FRILL, can demonstrate performance improvements, such as 32× faster and 40% the size of TRILL, with an average decrease in accuracy of only 2% over 7 diverse datasets. FRILL can also demonstrate performance improvements, such as 2.5× faster and 35% the size of TRILL-Distilled; (ii) an impact of performance optimization techniques like quantization-aware training, model compression, and architecture reductions on the latency, accuracy, and size of embedding models may be evaluated; and (iii) on-device representations may be bench-marked on two mobile-health tasks: a public dataset of human sounds, and detecting face-masked speech.

The FRILL Student-Model Architecture

The student models map log Mel-spectrograms to an embedding vector and are trained to mimic the TRILL representation described herein. In some embodiments, the student model architecture may include two components: a MobileNetV3 variant followed by a fully-connected bottleneck layer. The MobileNetV3 variant extracts rich information from inputted log Mel-spectrograms, and the bottleneck layer ensures a fixed embedding size. To explore the tradeoff between the performance and latency of the student models, a set of hyperparameters may be used as described below.
FRILL Architecture: MobileNet Size MobileNetV3 comprises two sizes: small and large. The small variant may be targeted toward resource-constrained applications and contains fewer inverted residual blocks and convolutional channels. In addition to these sizes, a truncated version of MobileNetV3Small may be adapted herein, named MobileNetV3Tiny, comprising the following modifications: (a) two of the eleven inverted residual blocks (blocks 6 and 11) from MobileNetV3Small may be removed. The choice of these blocks is based on the fact that these are duplicates of a preceding block; and (b) the number of channels in the final convolutional layer may be reduced from 1024 to 512.
FRILL Architecture: MobileNet Width MobileNet architectures feature a width multiplier α which modifies the number of channels in the convolutional layers within each inverted residual block. This hyperparameter is generally used to exchange model latency for performance.

FIG. 9 illustrates a table 900 with example values of hyperparameters to reduce size and latency, in accordance with example embodiments. In the first row, the entry under first column indicates a name of the architecture, such as "MV3Size" corresponding to a description "MobileNetV3 size" indicated in the entry under the second column, and with values "tiny, small, large," indicated in the entry under the third column. Additional rows indicate additional architectures.
FRILL Architecture: Global Average Pooling MobileNetV3 produces a set of two-dimensional feature maps at its output. When global average pooling (GAP) is disabled, these feature maps are flattened, concatenated, and passed to the bottleneck layer to produce an embedding. This concatenated vector is generally large, resulting in a sizable kernel in the bottleneck layer. GAP discards temporal information within an input audio window, which is less important for learning a non-semantic speech representation due to the fact non-lexical aspects of the speech signal (e.g. emotion, speaker identity) are more stable in time compared to lexical information. Accordingly, GAP may be used to reduce the size of the bottleneck layer kernel by taking the global average of all "pixels" in each output feature map, thus reducing the size of the bottleneck input.
FRILL Architecture: Bottleneck Layer Compression A significant portion of the student model weights are located in a kernel matrix of the bottleneck layer. To reduce the footprint of this layer, a compression operator based on Singular Value Decomposition (SVD) may be applied. The compression operator may learn a low-rank approximation of the bottleneck weight matrix $W^3$. Generally, low-rank approximations may be learned during training, as opposed to post-training. Formally, this operator uses SVD to generate matrices U and V such that the Frobenius norm of $W-UV^T$ can be minimized. The compressed kernel replaces a matrix of m×n weights with k (m+n) weights, where k is a hyperparameter that specifies the inner dimension of U and V, which we fix at k=100. A convex combination of original and compressed kernels may be used during training to produce the following layer output:

$$y = x(\lambda W + (1-\lambda)UV) + b \qquad \text{(Eqn. 2)}$$

where b is the bias vector in the bottleneck layer, x is the input vector, and λ is a scalar that is set to one at the beginning of training, and linearly decreases to zero over the first ten training epochs. Varying λ helps the optimizer transition to learning the weights of the compressed matrices. At inference time, λ may be set to zero and the original kernel may be discarded.
FRILL Architecture: Bottleneck Layer Quantization Quantization aims to reduce model footprint and latency by reducing the numerical precision of model weights. Instead of using post-training quantization which may cause performance degradation, Quantization-Aware Training (QAT) may be used. QAT is a procedure that gradually quantizes model weights during training. In some embodiments, a Tensorflow implementation of QAT may be utilized to quantize the bottleneck layer kernel from 32-bit floating point to 8-bits.

Experiments

An effect of each hyperparameter in the table of FIG. 9 on the representation quality, latency, and size of student embedding models may be determined. For each of 144 combinations of hyperparameters, the TRILL embedding may be distilled to a student network, the student embedding may be benchmarked by training simple classifiers to solve NOSS tasks and health tasks using embeddings as input features, and inference latency may be measured on a Pixel 1 smartphone. The distillation dataset, student network training procedure, NOSS benchmarking, and latency benchmarking procedures are as described in the following sections.

Distillation Dataset

To build a dataset for distillation, a 0.96-second audio context may be randomly sampled from each Audioset speech clip and a log-magnitude Mel spectrogram may be computed using a Short-Time Fourier Transform (STFT) window size and window stride of 25 ms and 10 ms respectively. In some experiments, 64 Mel bins may be computed. Using each spectrogram, the layer19 output of the TRILL model may be computed. Each pair, {log Mel spectrogram, layer19}, may be stored as a single observation for distillation training.

Student Model Training

Figure 10:
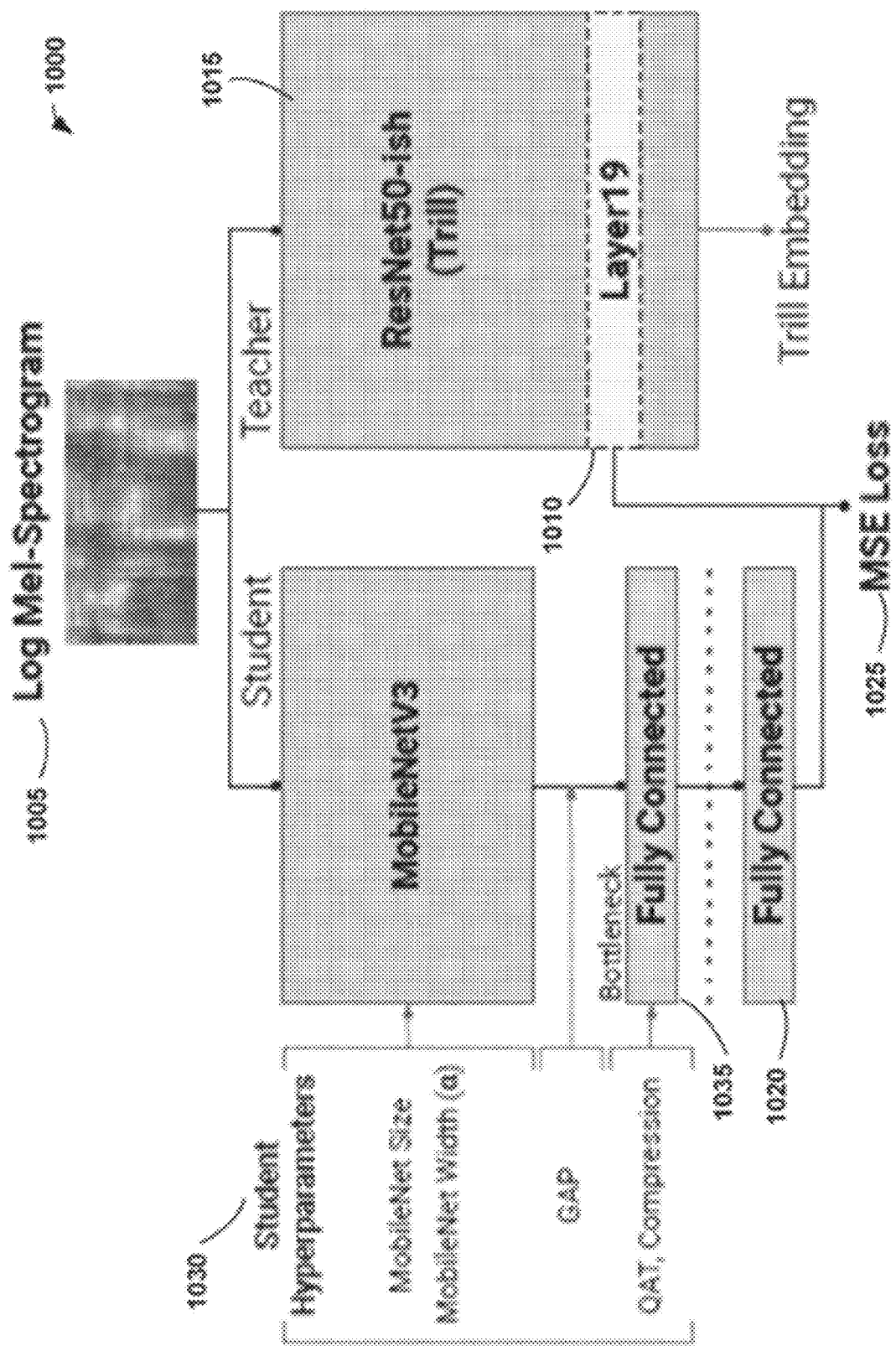
FIG. 10 illustrates an example training phase of a student model architecture, in accordance with example embodiments.

FIG. 10 illustrates an example training phase of a student model architecture, in accordance with example embodiments. A diagram of the training setup is shown in FIG. 10. Knowledge distillation for non-semantic speech embeddings is illustrated. Student models may be trained to map input Log Mel-spectrograms 1005 to the layer19 representation 1010 produced by a teacher model, TRILL 1015. Because the layer19 vector is much larger (12288d) than the student embeddings (2048d), an equal-length fully-connected layer 1020 may be appended to the output of the student model. This fully-connected layer 1020 enables computation of a mean-squared-error (MSE) loss 1025 against layer19 1010.

To train student models, a batch size of 128 and an initial learning rate of 1e-4 with an Adam optimizer may be used. In some embodiments, an exponential learning rate schedule may be used, with learning rates decreasing by a factor of 0.95 every 5,000 training steps. Each model may train for 50 epochs, or approximately 350,000 training steps. The dashed line shows the student model's output. As previously described, one or more student hyperparameters 1030 may be used to train the MobileNetV3 model, such as a width multiplier α, and a global average pooling (GAP) to reduce the size of the kernel of bottleneck layer 1035 by taking the global average of all "pixels" in each output feature map. Also, for example, a compression operator based on Singular Value Decomposition (SVD) may be applied to learn a low-rank approximation of the bottleneck weight matrix. As another example, Quantization-Aware Training (QAT) may be used to gradually quantizes model weights during the training.

NOSS Benchmark Analysis

To evaluate the quality of the student embeddings, a set of simple classifiers may be trained using embeddings as input features to solve each classification task in the NOSS benchmark. For each dataset in NOSS, a logistic regression, random forest, and linear discriminant analysis classifier may be trained using the SciKit-Learn library. Embeddings for each utterance may be averaged in time to produce a single feature vector. For tasks that contain multiple observations per speaker (SpeechCommands, CREMA-D, SAVEE), a set of classifiers using $L_2$ speaker normalization may be trained. Best test accuracy across combinations of downstream classifiers and normalization techniques may be determined. For example, accuracies on Dementia-Bank, one of the datasets included in the original NOSS benchmark, were all within 1% of each other.

Mobile Health-Sensing Tasks

In addition to tasks in the NOSS benchmark, Trill, Trill-Distilled, and each of the student models may be evaluated on a human sounds classification task and a face-mask speech detection task. The human sounds task is derived from the ESC-50 dataset, which contains 5-second sound clips from 50 classes. The human sounds subset of this dataset constitutes 10 of the 50 classes and includes labels such as 'coughing', 'sneezing', and 'breathing'. Similar to NOSS, a set of simple classifiers may be trained using input features from each student model and test accuracy may be reported on the best model. The first four published folds of ESC-50 may be used for training, and the fifth fold may be used for testing.

The objective of the mask speech task is to detect whether 1-second speech clips are from masked or unmasked speakers. The dataset contains around 19,000 masked and 18,000 unmasked speech examples. The performance of the models described herein may be evaluated as an indicator of their suitability for mobile health tasks.

Run-time Analysis

The TensorFlow Lite (TFLite) framework enables execution of machine learning models on mobile and edge devices. To measure the run-time performance of the student embeddings in their intended environment, each model may be converted to TFLite's flatbuffer file format for 32-bit floating-point execution and benchmark inference latency (single-threaded, CPU execution) on the Pixel 1 smartphone. Conversion to the flatbuffer format does not affect the quality of the representations. Latency measurements for TRILL and TRILL-Distilled may also be recorded for reference.

Results

Because student embeddings are evaluated on 7 datasets, it may be challenging to naturally rank models based on their "quality". Thus, an Aggregate Embedding Quality score may be determined by computing the performance difference between a student model and TRILL for each task, and averaging across tasks:

$$\text{Aggregate Embedding Quality}_m = \frac{1}{|D|} \sum_d (A_{md} - T_d) \quad \text{(Eqn. 3)}$$

where m indicates the student model, d indicates the dataset, and $T_d$ is the accuracy of TRILL on dataset $d \in D$. This score is indicative of an average deviation from TRILL's performance across all NOSS tasks and mobile health tasks.

To understand an impact each hyperparameter in the table of FIG. 9 has on the student models, a multivariate linear regression may be performed to model aggregate quality, latency, and size using model hyperparameters as predictors.

Each regression target may be standardized in order to produce regression weights on the same order of magnitude while preserving relative importance.

Figure 11:
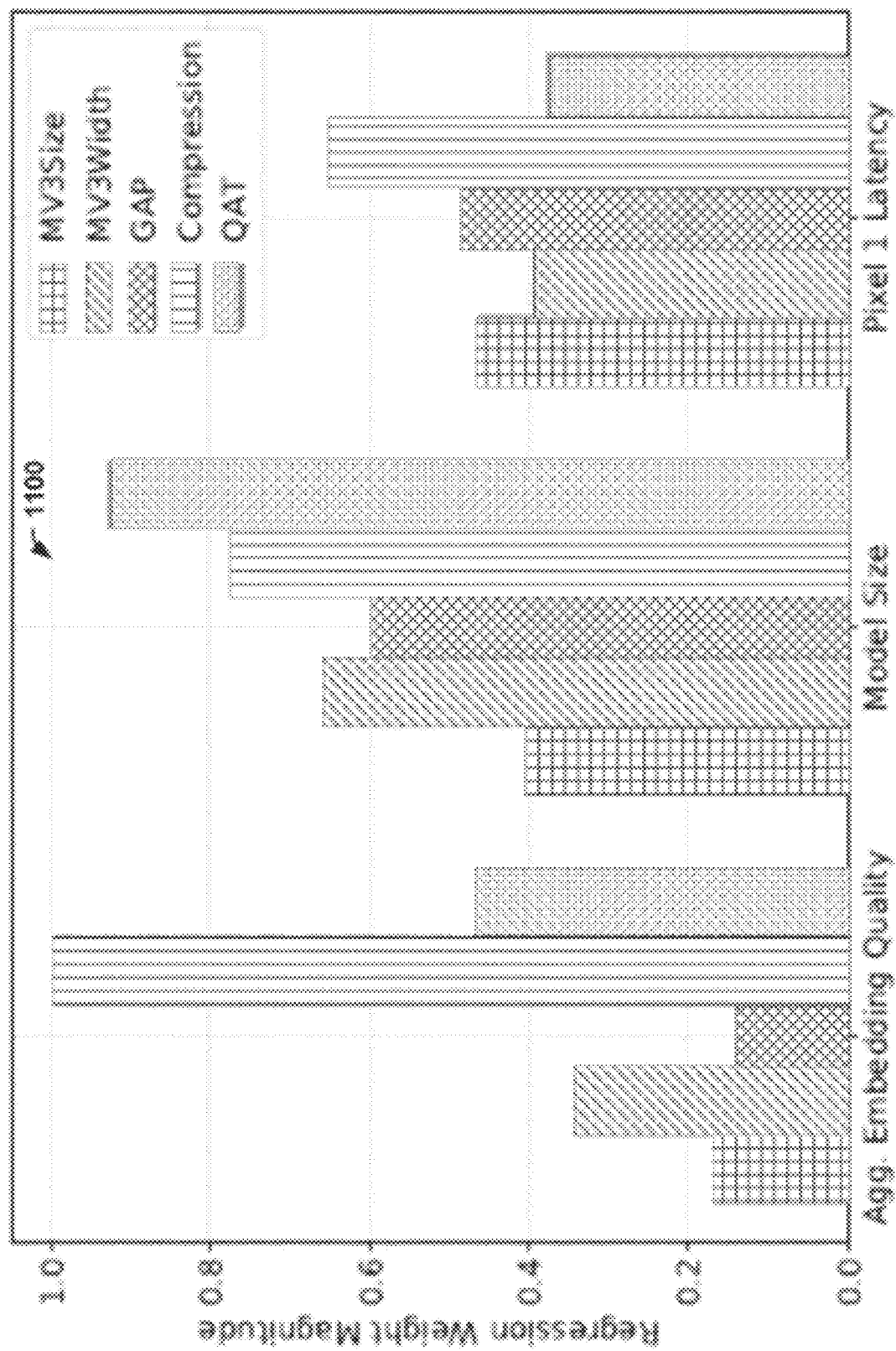
FIG. 11 illustrates a bar chart with magnitude of regression weights, in accordance with example embodiments.

FIG. 11 illustrates a bar chart 1100 with magnitude of regression weights, in accordance with example embodiments. Linear regression weight magnitudes for predicting model quality, latency, and size are illustrated along the vertical axis. The weights indicate the expected impact of changing the input hyperparameter. A higher weight magnitude indicates a greater expected impact. The horizontal axis shows comparative bar graphs for aggregate embedding quality, model size, and Pixel 1 latency, for each of the student hyperparameters 1030 such as MV3Size, MV3Width, GAP, Compression, and QAT, as described with reference to FIG. 10.

Figures 12, 13:
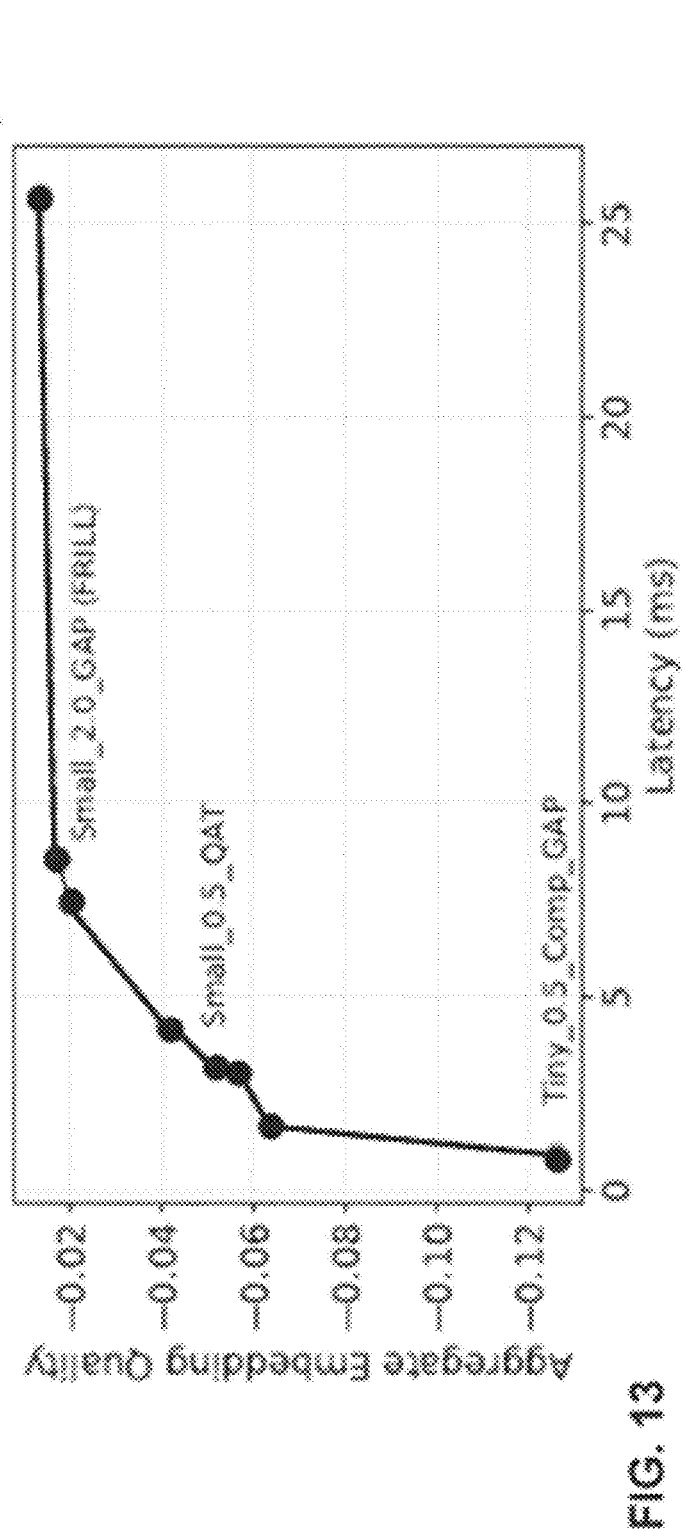
FIG. 12 illustrates non-semantic speech (NOSS) benchmark and mobile health task accuracies for three representative frontier models, in accordance with example embodiments.
FIG. 13 illustrates embedding quality and latency trade-off, in accordance with example embodiments.

FIG. 12 is a table 1200 illustrating NOSS benchmark and mobile health task accuracies for three representative frontier models, in accordance with example embodiments. Comparisons are shown with respect to TRILL (in the first row) and TRILL-Distilled (in the second row). The three representative frontier models are shown as Small_2.0_GAP (FRILL) (in the third row), Small_0.5_QAT (in the fourth row), and Tiny_0.5_Comp_GAP (in the fifth row). Test Performance on the NOSS Benchmark and Mobile Health Tasks are shown.

Observations

Architecture reduction techniques appear to have a smaller impact on performance and latency. For example, reducing MobileNetV3 size via α, by removing residual blocks, and by pooling early in the network had a smaller effect than QAT and bottleneck compression (see, FIG. 11). This suggests that the TRILL-Distilled Mobilenet part of the architecture may be likely over-parameterized compared to the representation quality possible by the bottleneck.

QAT appears to reduce model size the most, and latency the least. For example, QAT reduces overall model size the most and pixel 1 latency the least (see, FIG. 11). It decreases embedding quality by only half as much as compression, and is present in ⅛ of the best models.

Bottleneck compression appears to reduce embedding performance the most. This suggests that TRILL-Distilled's last bottleneck layer may be a highly performance-sensitive part of the model.

Quality/Latency Tradeoff

FIG. 13 illustrates embedding quality and latency tradeoff, in accordance with example embodiments. The horizontal axis represents an inference latency measured in milliseconds (ms), and the vertical axis represents an aggregate embedding quality, a difference in accuracy from TRILL's performance, averaged across benchmark datasets. To illustrate the latency and quality tradeoff in the presently described cohort of models (for example, models referenced in FIG. 12), a "quality" frontier plot 1300 may be generated. Plot 1300 is a sample of model performances and latencies on the quality/latency tradeoff curve. For all latency measurements l, the model with the best aggregate embedding quality with a latency less than or equal to one may be selected. This frontier, shown in FIG. 13, features 8 student models of various qualities and latencies.

As illustrated, FRILL (fast TRILL), has an aggregate embedding quality score of 0.0169, indicating an average deviation from TRILL quality of 1.69% with respect to the datasets in this study. FRILL has an inference latency of 8.5 ms on a Pixel 1 smartphone, and is only 38.5 megabytes in the TFLite file format.

After eliminating models with better and faster alternatives, 8 "frontier" models may be reviewed. The fastest model appears to run at 0.9 ms, which is 300× faster than TRILL and 25× faster than TRILL-Distilled. FRILL appears to run at 8.5 ms, which is about 32× faster than TRILL 2.5× faster than TRILL-Distilled. FRILL also appears to be roughly 40% the size of TRILL and TRILL-Distilled. The plot 1300 is steep on both sides of the frontier. This may mean that with minimal latency costs, much better performance may be achieved on one end, and vice versa on the other. This supports the choice of experiment hyperparameters. Though there is a frontier model with an aggregate embedding quality higher than FRILL, it comes at the cost of a significant bump in latency.

As described in various embodiments, an efficient non-semantic speech embedding model trained via knowledge distillation is described, that is fast enough to be run in real-time on a mobile device. Latency and size reduction techniques are described, and their impact on model quality is quantified. Performance/latency tradeoff curve for the 144 trained models is analyzed, and size, latency, and performance numbers are reported for representative models. In particular, FRILL appears to exhibit a 32× inference speedup and 60% size reduction, with an average decrease in accuracy of less than 2% over 7 different datasets, as compared to the TRILL model. FRILL appears to be 2.5× faster and 35% the size of TRILL-Distilled. Effectiveness of the embeddings on two new mobile health tasks are evaluated. These new tasks in particular benefit from the on-device nature of the embeddings, since performing computations locally can improve both the privacy and latency of resulting models.

Training Machine Learning Methods for Generating Inferences/Predictions

Figure 14:
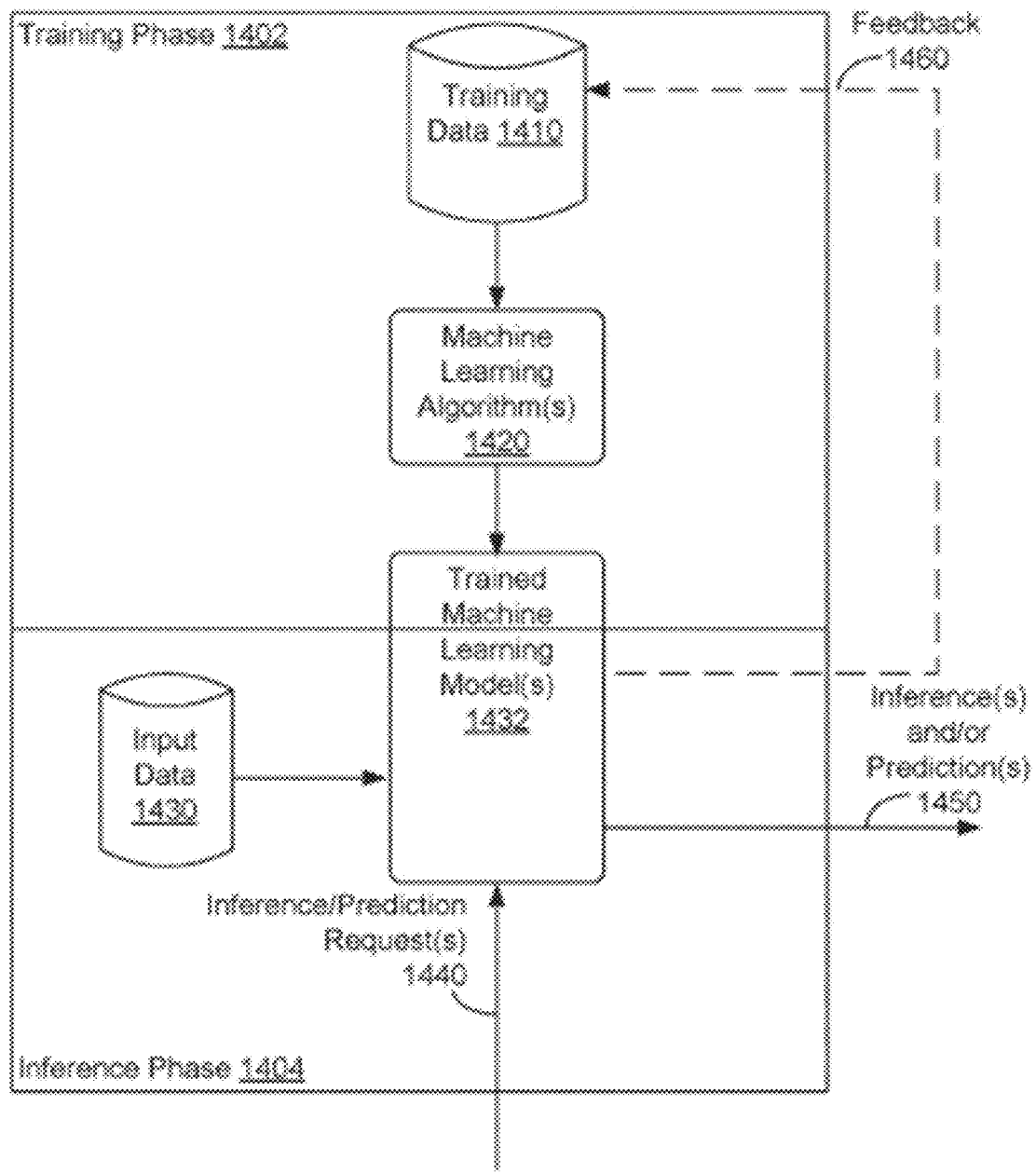
FIG. 14 is a diagram illustrating training and inference phases of a machine learning model, in accordance with example embodiments.

FIG. 14 shows diagram 1400 illustrating a training phase 1402 and an inference phase 1404 of trained machine learning model(s) 1432, in accordance with example embodiments. Some machine learning techniques involve training one or more machine learning algorithms on an input set of training data to recognize patterns in the training data and provide output inferences and/or predictions about (patterns in the) training data. The resulting trained machine learning algorithm can be termed as a trained machine learning model. For example, FIG. 14 shows training phase 1402 where one or more machine learning algorithms 1420 are being trained on training data 1410 to become trained machine learning model 1432. Then, during inference phase 1404, trained machine learning model 1432 can receive input data 1430 and one or more inference/prediction requests 1440 (perhaps as part of input data 1430) and responsively provide as an output one or more inferences and/or predictions 1450.

As such, trained machine learning model(s) 1432 can include one or more models of one or more machine learning algorithms 1420. Machine learning algorithm(s) 1420 may include, but are not limited to: an artificial neural network (e.g., convolutional neural networks, a recurrent neural network, a Bayesian network, a hidden Markov model, a Markov decision process, a logistic regression function, a support vector machine, a suitable statistical machine learning algorithm, and/or a heuristic machine learning system). Machine learning algorithm(s) 1420 may be supervised or unsupervised, and may implement any suitable combination of online and offline learning.

In some examples, machine learning algorithm(s) 1420 and/or trained machine learning model(s) 1432 can be accelerated using on-device coprocessors, such as graphic processing units (GPUs), tensor processing units (TPUs), digital signal processors (DSPs), and/or application specific integrated circuits (ASICs). Such on-device coprocessors can be used to speed up machine learning algorithm(s) 1420 and/or trained machine learning model(s) 1432. In some examples, trained machine learning model(s) 1432 can be trained, resident, and executed to provide inferences on a particular computing device, and/or otherwise can make inferences for the particular computing device.

During training phase 1402, machine learning algorithm(s) 1420 can be trained by providing at least training data 1410 as training input using unsupervised, supervised, semi-supervised, and/or reinforcement learning techniques. Training data 1410 can include a plurality of speech audio clips from a speech dataset. Unsupervised learning involves providing a portion (or all) of training data 1410 to machine learning algorithm(s) 1420 and machine learning algorithm(s) 1420 determining one or more output inferences based on the provided portion (or all) of training data 1410. Supervised learning involves providing a portion of training data 1410 to machine learning algorithm(s) 1420, with machine learning algorithm(s) 1420 determining one or more output inferences based on the provided portion of training data 1410, and the output inference(s) are either accepted or corrected based on correct results associated with training data 1410. In some examples, supervised learning of machine learning algorithm(s) 1420 can be governed by a set of rules and/or a set of labels for the training input, and the set of rules and/or set of labels may be used to correct inferences of machine learning algorithm(s) 1420.

Semi-supervised learning involves having correct results for part, but not all, of training data 1410. During semi-supervised learning, supervised learning is used for a portion of training data 1410 having correct results, and unsupervised learning is used for a portion of training data 1410 not having correct results. Reinforcement learning involves machine learning algorithm(s) 1420 receiving a reward signal regarding a prior inference, where the reward signal can be a numerical value. During reinforcement learning, machine learning algorithm(s) 1420 can output an inference and receive a reward signal in response, where machine learning algorithm(s) 1420 are configured to try to maximize the numerical value of the reward signal. In some examples, reinforcement learning also utilizes a value function that provides a numerical value representing an expected total of the numerical values provided by the reward signal over time. In some examples, machine learning algorithm(s) 1420 and/or trained machine learning model(s) 1432 can be trained using other machine learning techniques, including but not limited to, incremental learning and curriculum learning.

In some examples, machine learning algorithm(s) 1420 and/or trained machine learning model(s) 1432 can use transfer learning techniques. For example, transfer learning techniques can involve trained machine learning model(s) 1432 being pre-trained on one set of data and additionally trained using training data 1410. More particularly, machine learning algorithm(s) 1420 can be pre-trained on data from one or more computing devices and a resulting trained machine learning model provided to a particular computing device, where the particular computing device is intended to execute the trained machine learning model during inference phase 1404. Then, during training phase 1402, the pre-trained machine learning model can be additionally trained using training data 1410, where training data 1410 can be derived from kernel and non-kernel data of the particular computing device. This further training of the machine learning algorithm(s) 1420 and/or the pre-trained machine learning model using training data 1410 of the particular computing device's data can be performed using either supervised or unsupervised learning. Once machine learning algorithm(s) 1420 and/or the pre-trained machine learning model has been trained on at least training data 1410, training phase 1402 can be completed. The trained resulting machine learning model can be utilized as at least one of trained machine learning model(s) 1432.

In particular, once training phase 1402 has been completed, trained machine learning model(s) 1432 can be provided to a computing device, if not already on the computing device. Inference phase 1404 can begin after trained machine learning model(s) 1432 are provided to the particular computing device.

During inference phase 1404, trained machine learning model(s) 1432 can receive input data 1430 and generate and output one or more corresponding inferences and/or predictions 1450 about input data 1430. As such, input data 1430 can be used as an input to trained machine learning model(s) 1432 for providing corresponding inference(s) and/or prediction(s) 1450 to kernel components and non-kernel components. For example, trained machine learning model(s) 1432 can generate inference(s) and/or prediction(s) 1450 in response to one or more inference/prediction requests 1440. In some examples, trained machine learning model(s) 1432 can be executed by a portion of other software. For example, trained machine learning model(s) 1432 can be executed by an inference or prediction daemon to be readily available to provide inferences and/or predictions upon request. Input data 1430 can include data from the particular computing device executing trained machine learning model(s) 1432 and/or input data from one or more computing devices other than the particular computing device.

Input data 1430 can include an audio stream to generate an input audio sequence comprising a plurality of time-separated audio segments.

Inference(s) and/or prediction(s) 1450 can include output cough metrics for each of cough episodes detected in the input audio sequence, and/or other output data produced by trained machine learning model(s) 1432 operating on input data 1430 (and training data 1410). In some examples, trained machine learning model(s) 1432 can use output inference(s) and/or prediction(s) 1450 as input feedback 1460. Trained machine learning model(s) 1432 can also rely on past inferences as inputs for generating new inferences.

In some examples, a single computing device ("CD_SOLO") can include the trained version of the machine learning model, perhaps after training the machine learning model. Then, computing device CD_SOLO can receive requests to detect a cough in an audio stream, and use the trained version of the machine learning model to generate cough metrics for each cough episode detected in the input audio sequence.

In some examples, two or more computing devices, such as a first client device ("CD_CLI") and a server device ("CD_SRV") can be used to provide the output; e.g., a first computing device CD_CLI can generate and send requests to detect a cough in an audio stream to a second computing device CD_SRV. Then, CD_SRV can use the trained version of the machine learning model, to generate cough metrics for each cough episode detected in the input audio sequence. Then, upon reception of responses to the requests, CD_CLI can provide the requested output via one or more control interfaces (e.g., using a user interface and/or a display, a printed copy, an electronic communication, etc.).

Example Data Network

Figure 15:
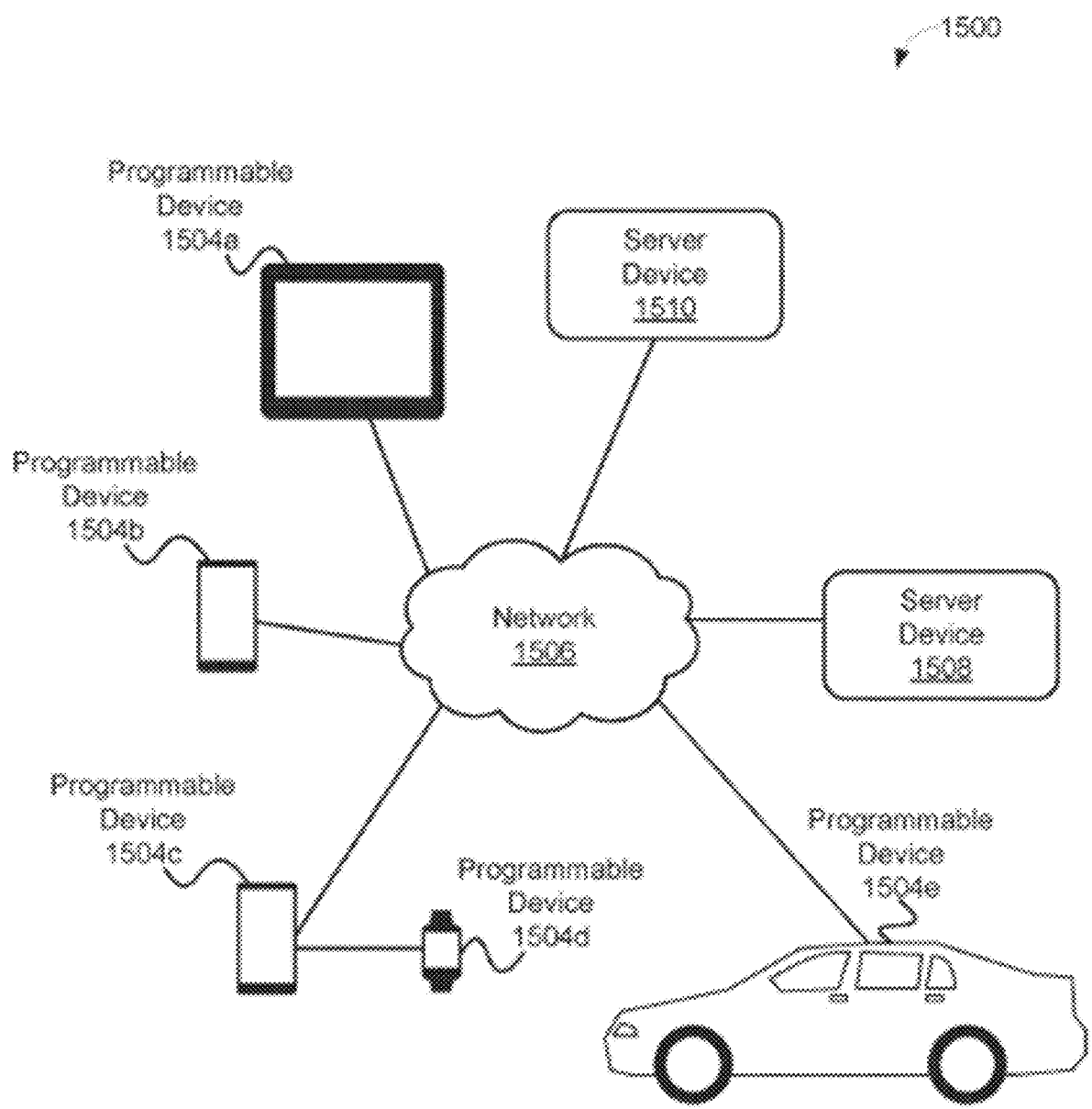
FIG. 15 depicts a distributed computing architecture, in accordance with example embodiments.

FIG. 15 depicts a distributed computing architecture 1500, in accordance with example embodiments. Distributed computing architecture 1500 includes server devices 1508, 1510 that are configured to communicate, via network 1506, with programmable devices 1504a, 1504b, 1504c, 1504d, 1504e. Network 1506 may correspond to a local area network (LAN), a wide area network (WAN), a WLAN, a WWAN, a corporate intranet, the public Internet, or any other type of network configured to provide a communications path between networked computing devices. Network 1506 may also correspond to a combination of one or more LANs, WANs, corporate intranets, and/or the public Internet.

Although FIG. 15 only shows five programmable devices, distributed application architectures may serve tens, hundreds, or thousands of programmable devices. Moreover, programmable devices 1504a, 1504b, 1504c, 1504d, 1504e (or any additional programmable devices) may be any sort of computing device, such as a mobile computing device, desktop computer, wearable computing device, head-mountable device (HMD), network terminal, a mobile computing device, and so on. In some examples, such as illustrated by programmable devices 1504a, 1504b, 1504c, 1504e, programmable devices can be directly connected to network 1506. In other examples, such as illustrated by programmable device 1504d, programmable devices can be indirectly connected to network 1506 via an associated computing device, such as programmable device 1504c. In this example, programmable device 1504c can act as an associated computing device to pass electronic communications between programmable device 1504d and network 1506. In other examples, such as illustrated by programmable device 1504e, a computing device can be part of and/or inside a vehicle, such as a car, a truck, a bus, a boat or ship, an airplane, etc. In other examples not shown in FIG. 15, a programmable device can be both directly and indirectly connected to network 1506.

Server devices 1508, 1510 can be configured to perform one or more services, as requested by programmable devices 1504a-1504e. For example, server device 1508 and/or 1510 can provide content to programmable devices 1504a-1504e. The content can include, but is not limited to, web pages, hypertext, scripts, binary data such as compiled software, images, audio, and/or video. The content can include compressed and/or uncompressed content. The content can be encrypted and/or unencrypted. Other types of content are possible as well.

As another example, server devices 1508 and/or 1510 can provide programmable devices 1504a-1504e with access to software for database, search, computation, graphical, audio, video, World Wide Web/Internet utilization, and/or other functions. Many other examples of server devices are possible as well.

Computing Device Architecture

Figure 16:
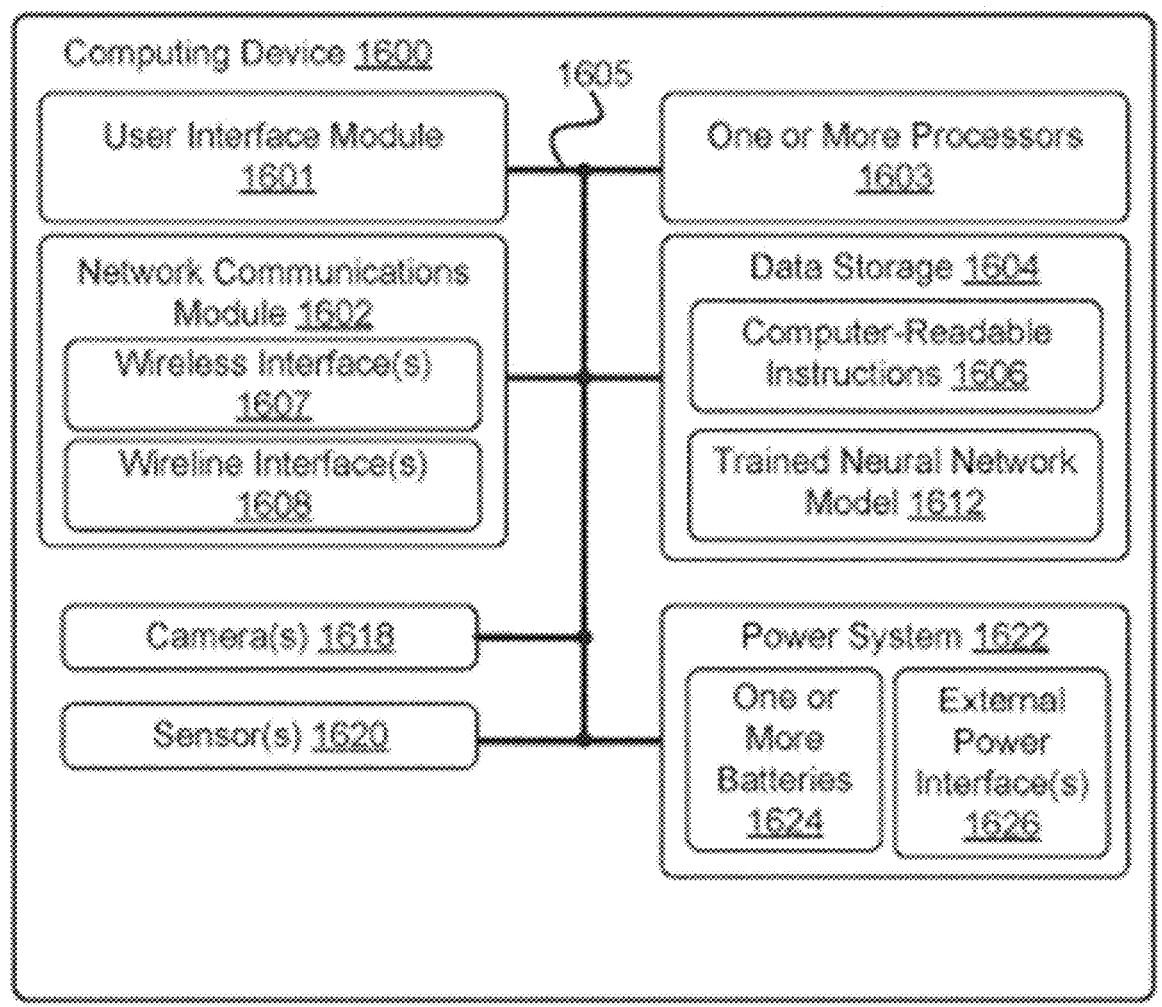
FIG. 16 is a block diagram of a computing device, in accordance with example embodiments.

FIG. 16 is a block diagram of an example computing device 1600, in accordance with example embodiments. In particular, computing device 1600 shown in FIG. 16 can be configured to perform at least one function of and/or related to neural network 1000, and/or methods 1800, and/or 1900.

Computing device 1600 may include a user interface module 1601, a network communications module 1602, one or more processors 1603, data storage 1604, one or more cameras 1618, one or more sensors 1620, and power system 1622, all of which may be linked together via a system bus, network, or other connection mechanism 1605.

User interface module 1601 can be operable to send data to and/or receive data from external user input/output devices. For example, user interface module 1601 can be configured to send and/or receive data to and/or from user input devices such as a touch screen, a computer mouse, a keyboard, a keypad, a touch pad, a trackball, a joystick, a voice recognition module, and/or other similar devices. User interface module 1601 can also be configured to provide output to user display devices, such as one or more cathode ray tubes (CRT), liquid crystal displays, light emitting diodes (LEDs), displays using digital light processing (DLP) technology, printers, light bulbs, and/or other similar devices, either now known or later developed. User interface module 1601 can also be configured to generate audible outputs, with devices such as a speaker, speaker jack, audio output port, audio output device, earphones, and/or other similar devices. User interface module 1601 can further be configured with one or more haptic devices that can generate haptic outputs, such as vibrations and/or other outputs detectable by touch and/or physical contact with computing device 1600. In some examples, user interface module 1601 can be used to provide a graphical user interface (GUI) for utilizing computing device 1600.

Network communications module 1602 can include one or more devices that provide one or more wireless interfaces 1607 and/or one or more wireline interfaces 1608 that are configurable to communicate via a network. Wireless interface(s) 1607 can include one or more wireless transmitters, receivers, and/or transceivers, such as a Bluetooth™ transceiver, a Zigbee® transceiver, a Wi-Fi™ transceiver, a WiMAX™ transceiver, an LTE™ transceiver, and/or other type of wireless transceiver configurable to communicate via a wireless network. Wireline interface(s) 1608 can include one or more wireline transmitters, receivers, and/or transceivers, such as an Ethernet transceiver, a Universal Serial Bus (USB) transceiver, or similar transceiver configurable to communicate via a twisted pair wire, a coaxial cable, a fiber-optic link, or a similar physical connection to a wireline network.

In some examples, network communications module 1602 can be configured to provide reliable, secured, and/or authenticated communications. For each communication described herein, information for facilitating reliable communications (e.g., guaranteed message delivery) can be provided, perhaps as part of a message header and/or footer (e.g., packet/message sequencing information, encapsulation headers and/or footers, size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, Data Encryption Standard (DES), Advanced Encryption Standard (AES), a Rivest-Shamir-Adelman (RSA) algorithm, a Diffie-Hellman algorithm, a secure sockets protocol such as Secure Sockets Layer (SSL) or Transport Layer Security (TLS), and/or Digital Signature Algorithm (DSA). Other cryptographic protocols and/or algorithms can be used as well or in addition to those listed herein to secure (and then decrypt/decode) communications.

One or more processors 1603 can include one or more general purpose processors, and/or one or more special purpose processors (e.g., digital signal processors, tensor processing units (TPUs), graphics processing units (GPUs), application specific integrated circuits, etc.). One or more processors 1603 can be configured to execute computer-readable instructions 1606 that are contained in data storage 1604 and/or other instructions as described herein.

Data storage 1604 can include one or more non-transitory computer-readable storage media that can be read and/or accessed by at least one of one or more processors 1603. The one or more computer-readable storage media can include volatile and/or non-volatile storage components, such as optical, magnetic, organic or other memory or disc storage, which can be integrated in whole or in part with at least one of one or more processors 1603. In some examples, data storage 1604 can be implemented using a single physical device (e.g., one optical, magnetic, organic or other memory or disc storage unit), while in other examples, data storage 1604 can be implemented using two or more physical devices.

Data storage 1604 can include computer-readable instructions 1606 and perhaps additional data. In some examples, data storage 1604 can include storage required to perform at least part of the herein-described methods, scenarios, and techniques and/or at least part of the functionality of the herein-described devices and networks. In some examples, data storage 1604 can include storage for a trained neural network model 1612 (e.g., a model of trained convolutional neural networks such as convolutional neural networks 140). In particular of these examples, computer-readable instructions 1606 can include instructions that, when executed by processor(s) 1603, enable computing device 1600 to provide for some or all of the functionality of trained neural network model 1612.

In some examples, computing device 1600 can include one or more cameras 1618. Camera(s) 1618 can include one or more image capture devices, such as still and/or video cameras, equipped to capture light and record the captured light in one or more images; that is, camera(s) 1618 can generate image(s) of captured light. The one or more images can be one or more still images and/or one or more images utilized in video imagery. Camera(s) 1618 can capture light and/or electromagnetic radiation emitted as visible light, infrared radiation, ultraviolet light, and/or as one or more other frequencies of light.

In some examples, computing device 1600 can include one or more sensors 1620. Sensors 1620 can be configured to measure conditions within computing device 1600 and/or conditions in an environment of computing device 1600 and provide data about these conditions. For example, sensors 1620 can include one or more of: (i) sensors for obtaining data about computing device 1600, such as, but not limited to, a thermometer for measuring a temperature of computing device 1600, a battery sensor for measuring power of one or more batteries of power system 1622, and/or other sensors measuring conditions of computing device 1600; (ii) an identification sensor to identify other objects and/or devices, such as, but not limited to, a Radio Frequency Identification (RFID) reader, proximity sensor, one-dimensional barcode reader, two-dimensional barcode (e.g., Quick Response (QR) code) reader, and a laser tracker, where the identification sensors can be configured to read identifiers, such as RFID tags, barcodes, QR codes, and/or other devices and/or object configured to be read and provide at least identifying information; (iii) sensors to measure locations and/or movements of computing device 1600, such as, but not limited to, a tilt sensor, a gyroscope, an accelerometer, a Doppler sensor, a GPS device, a sonar sensor, a radar device, a laser-displacement sensor, and a compass; (iv) an environmental sensor to obtain data indicative of an environment of computing device 1600, such as, but not limited to, an infrared sensor, an optical sensor, a light sensor, a biosensor, a capacitive sensor, a touch sensor, a temperature sensor, a wireless sensor, a radio sensor, a movement sensor, a microphone, a sound sensor, an ultrasound sensor and/or a smoke sensor; and/or (v) a force sensor to measure one or more forces (e.g., inertial forces and/or G-forces) acting about computing device 1600, such as, but not limited to one or more sensors that measure: forces in one or more dimensions, torque, ground force, friction, and/or a zero moment point (ZMP) sensor that identifies ZMPs and/or locations of the ZMPs. Many other examples of sensors 1620 are possible as well.

Power system 1622 can include one or more batteries 1624 and/or one or more external power interfaces 1626 for providing electrical power to computing device 1600. Each battery of the one or more batteries 1624 can, when electrically coupled to the computing device 1600, act as a source of stored electrical power for computing device 1600. One or more batteries 1624 of power system 1622 can be configured to be portable. Some or all of one or more batteries 1624 can be readily removable from computing device 1600. In other examples, some or all of one or more batteries 1624 can be internal to computing device 1600, and so may not be readily removable from computing device 1600. Some or all of one or more batteries 1624 can be rechargeable. For example, a rechargeable battery can be recharged via a wired connection between the battery and another power supply, such as by one or more power supplies that are external to computing device 1600 and connected to computing device 1600 via the one or more external power interfaces. In other examples, some or all of one or more batteries 1624 can be non-rechargeable batteries.

One or more external power interfaces 1626 of power system 1622 can include one or more wired-power interfaces, such as a USB cable and/or a power cord, that enable wired electrical power connections to one or more power supplies that are external to computing device 1600. One or more external power interfaces 1626 can include one or more wireless power interfaces, such as a Qi wireless charger, that enable wireless electrical power connections, such as via a Qi wireless charger, to one or more external power supplies. Once an electrical power connection is established to an external power source using one or more external power interfaces 1626, computing device 1600 can draw electrical power from the external power source the established electrical power connection. In some examples, power system 1622 can include related sensors, such as battery sensors associated with one or more batteries or other types of electrical power sensors.

Cloud-Based Servers

Figure 17:
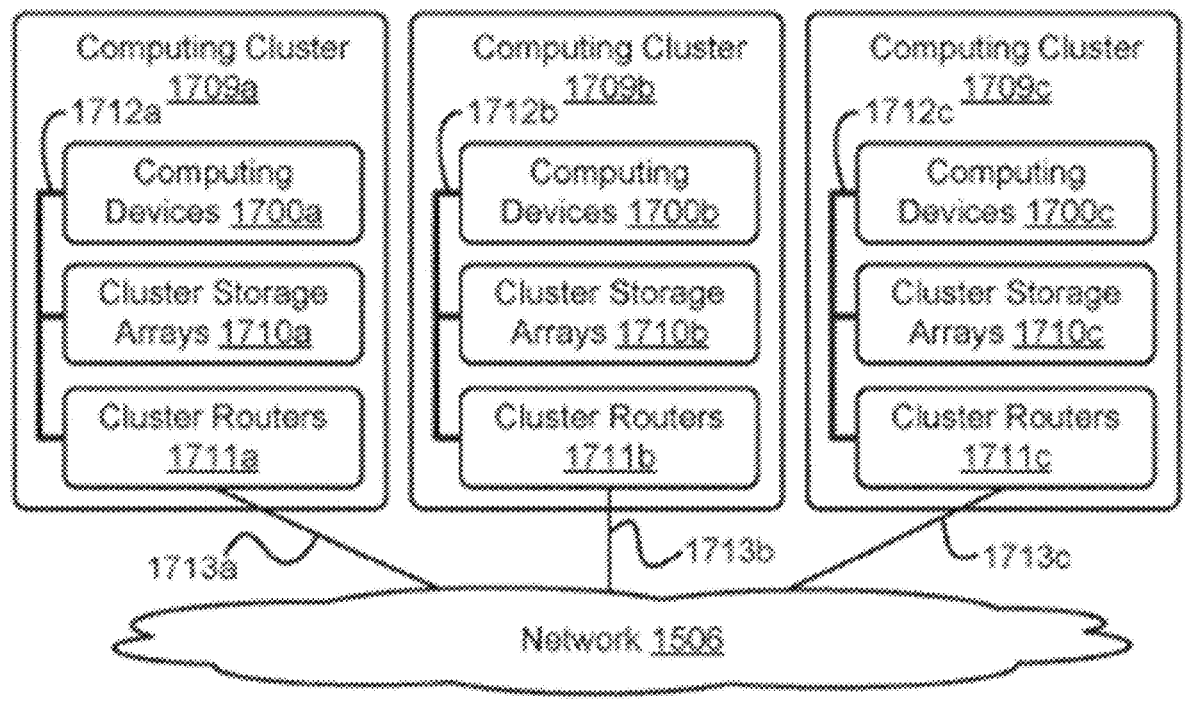
FIG. 17 depicts a network of computing clusters arranged as a cloud-based server system, in accordance with example embodiments.

FIG. 17 depicts a network 1506 of computing clusters 1709a, 1709b, 1709c arranged as a cloud-based server system in accordance with an example embodiment. Computing clusters 1709a, 1709b, and 1709c can be cloud-based devices that store program logic and/or data of cloud-based applications and/or services; e.g., perform at least one function of and/or related to neural networks 1000, and/or methods 1800, and/or 1900.

In some embodiments, computing clusters 1709a, 1709b, and 1709c can be a single computing device residing in a single computing center. In other embodiments, computing clusters 1709a, 1709b, and 1709c can include multiple computing devices in a single computing center, or even multiple computing devices located in multiple computing centers located in diverse geographic locations. For example, FIG. 17 depicts each of computing clusters 1709a, 1709b, and 1709c residing in different physical locations.

In some embodiments, data and services at computing clusters 1709a, 1709b, 1709c can be encoded as computer readable information stored in non-transitory, tangible computer readable media (or computer readable storage media) and accessible by other computing devices. In some embodiments, computing clusters 1709a, 1709b, 1709c can be stored on a single disk drive or other tangible storage media, or can be implemented on multiple disk drives or other tangible storage media located at one or more diverse geographic locations.

In FIG. 17, functionality of neural networks 1000, and/or a computing device can be distributed among computing clusters 1709a, 1709b, 1709c. Computing cluster 1709a can include one or more computing devices 1700a, cluster storage arrays 1710a, and cluster routers 1711a connected by a local cluster network 1712a. Similarly, computing cluster 1709b can include one or more computing devices 1700b, cluster storage arrays 1710b, and cluster routers 1711b connected by a local cluster network 1712b. Likewise, computing cluster 1709c can include one or more computing devices 1700c, cluster storage arrays 1710c, and cluster routers 1711c connected by a local cluster network 1712c.

In some embodiments, each of computing clusters 1709a, 1709b, and 1709c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 1709a, for example, computing devices 1700a can be configured to perform various computing tasks of convolutional neural network, and/or a computing device. In one embodiment, the various functionalities of a convolutional neural network, and/or a computing device can be distributed among one or more of computing devices 1700a, 1700b, and 1700c. Computing devices 1700b and 1700c in respective computing clusters 1709b and 1709c can be configured similarly to computing devices 1700a in computing cluster 1709a. On the other hand, in some embodiments, computing devices 1700a, 1700b, and 1700c can be configured to perform different functions.

In some embodiments, computing tasks and stored data associated with a convolutional neural networks, and/or a computing device can be distributed across computing devices 1700a, 1700b, and 1700c based at least in part on the processing requirements of convolutional neural networks, and/or a computing device, the processing capabilities of computing devices 1700a, 1700b, 1700c, the latency of the network links between the computing devices in each computing cluster and between the computing clusters themselves, and/or other factors that can contribute to the cost, speed, fault-tolerance, resiliency, efficiency, and/or other design goals of the overall system architecture.

Cluster storage arrays 1710a, 1710b, 1710c of computing clusters 1709a, 1709b, and 1709c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of convolutional neural networks, and/or a computing device can be distributed across computing devices 1700a, 1700b, 1700c of computing clusters 1709a, 1709b, 1709c, various active portions and/or backup portions of these components can be distributed across cluster storage arrays 1710a, 1710b, 1710c. For example, some cluster storage arrays can be configured to store one portion of the data of a convolutional neural network, and/or a computing device, while other cluster storage arrays can store other portion(s) of data of a convolutional neural network, and/or a computing device. Also, for example, some cluster storage arrays can be configured to store the data of a first convolutional neural network, while other cluster storage arrays can store the data of a second and/or third convolutional neural network. Additionally, some cluster storage arrays can be configured to store backup versions of data stored in other cluster storage arrays.

Cluster routers 1711a, 1711b, 1711c in computing clusters 1709a, 1709b, and 1709c can include networking equipment configured to provide internal and external communications for the computing clusters. For example, cluster routers 1711a in computing cluster 1709a can include one or more interne switching and routing devices configured to provide (i) local area network communications between computing devices 1700a and cluster storage arrays 1710a via local cluster network 1712a, and (ii) wide area network communications between computing cluster 1709a and computing clusters 1709b and 1709c via wide area network link 1713a to network 1506. Cluster routers 1711b and 1711c can include network equipment similar to cluster routers 1711a, and cluster routers 1711b and 1711c can perform similar networking functions for computing clusters 1709b and 1709b that cluster routers 1711a perform for computing cluster 1709a.

In some embodiments, the configuration of cluster routers 1711a, 1711b, 1711c can be based at least in part on the data communication requirements of the computing devices and cluster storage arrays, the data communications capabilities of the network equipment in cluster routers 1711a, 1711b, 1711c, the latency and throughput of local cluster networks 1712a, 1712b, 1712c, the latency, throughput, and cost of wide area network links 1713a, 1713b, 1713c, and/or other factors that can contribute to the cost, speed, fault-tolerance, resiliency, efficiency and/or other design criteria of the moderation system architecture.

Example Methods of Operation

FIG. 18 illustrates flow chart 1800 of operations related to detecting a cough in an audio stream. The operations may be executed by and/or used with any of computing devices 1600, or other ones of the preceding example embodiments.

Block 1810 involves performing one or more pre-processing steps on the audio stream to generate an input audio sequence comprising a plurality of time-separated audio segments.

Block 1820 involves generating an embedding for each of the segments of the input audio sequence using an audio feature set generated by a self-supervised triplet loss embedding model, the embedding model having been trained to learn the audio feature set in a self-supervised triplet loss manner from a plurality of speech audio clips from a speech dataset.

Block 1830 involves providing the embedding for each of the segments to a model performing cough detection inference, the model generating a probability that each of the segments of the input audio sequence includes a cough episode.

Block 1840 involves generating cough metrics for each of the cough episodes detected in the input audio sequence.

Some embodiments involve instructing a user generating the audio stream to conduct a calibration procedure in which the user is instructed to cough N times. Such embodiments also involve computing an embedding for each detected cough using the audio feature set. Such embodiments further involve computing a similarity or the equivalent between each pairwise combination of the N coughs. Such embodiments additionally involve determining a verification threshold for the model performing cough detection inference based on the computed similarities.

Some embodiments involve characterizing the cough based on the cough metrics.

In some embodiments, the cough metrics may include at least one of: a) a number of cough episodes per segment, b) a number of cough episodes in the input audio sequence; c) a duration of the cough episode(s) per segment; or d) a duration of the cough episode(s) in the input audio sequence.

Some embodiments involve performing a cough-type classification of one or more cough episodes detected in the input data.

Some embodiments involve training the self-supervised triplet loss embedding model to learn the audio feature set in the self-supervised triplet loss manner from the plurality of speech audio clips from the speech dataset, and responsively generate the audio feature set in the form of a multidimensional vector.

In some embodiments, the generating of the embedding involves applying the self-supervised triplet loss embedding model by utilizing temporal proximity in the speech data as a self-supervision signal.

In some embodiments, the generating of the embedding involves applying the self-supervised triplet loss embedding model by applying knowledge distillation to the embedding model, and wherein the embedding model is further configured based on one or more of: (i) varying a number filters in each layer of the model, (ii) reducing a size of a bottleneck layer kernel by computing a global average over pixels in each output feature map, (iii) applying a compression operator to a bottleneck layer, wherein the compression operator is based on a Singular Value Decomposition (SVD) that is configured to learn a low-rank approximation of a weight matrix associated with the bottleneck layer, or (iv) applying Quantization-Aware training (QAT) that is configured to gradually reduce a numerical precision of weights associated with a bottleneck layer during training.

FIG. 19 illustrates flow chart 1900 of operations related to detecting a non-semantic, paralinguistic event in an audio stream. The operations may be executed by and/or used with any of computing devices 1600, or other ones of the preceding example embodiments.

Block 1910 involves performing one or more pre-processing steps on the audio stream to generate an input audio sequence comprising a plurality of time-separated audio segments.

Block 1920 involves generating an embedding for each of the segments of the input audio sequence using an audio feature set generated by a self-supervised triplet loss embedding model, the embedding model having been trained to learn the audio feature set in a self-supervised triplet loss manner from a plurality of speech audio clips from a speech dataset.

Block 1930 involves providing the embedding for each of the segments to a model performing inference to detect the non-semantic, paralinguistic event, the model generating a probability that each of the segments of the input audio sequence includes such an event.

Some embodiments involve generating metrics for each of the non-semantic paralinguistic events detected in the input audio sequence.

In some embodiments, the non-semantic, paralinguistic event involves a determination of whether the audio stream contains speech from a person wearing a mask.

In some embodiments, the non-semantic, paralinguistic event includes one or more of snoring, wheezing, or a hiccup.

Some embodiments involve training the self-supervised triplet loss embedding model to learn the audio feature set in the self-supervised triplet loss manner from the plurality of speech audio clips from the speech dataset, and responsively generate the audio feature set in the form of a multidimensional vector.

In some embodiments, the generating of the embedding involves applying the self-supervised triplet loss embedding model by utilizing temporal proximity in the speech data as a self-supervision signal.

In some embodiments, the generating of the embedding involves applying the self-supervised triplet loss embedding model by applying knowledge distillation to the embedding model, and wherein the embedding model is further configured based on one or more of: (i) varying a number filters in each layer of the model, (ii) reducing a size of a bottleneck layer kernel by computing a global average over pixels in each output feature map, (iii) applying a compression operator to a bottleneck layer, wherein the compression operator is based on a Singular Value Decomposition (SVD) that is configured to learn a low-rank approximation of a weight matrix associated with the bottleneck layer, or (iv) applying Quantization-Aware training (QAT) that is configured to gradually reduce a numerical precision of weights associated with a bottleneck layer during training.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as non-transitory computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are provided for explanatory purposes and are not intended to be limiting, with the true scope being indicated by the following claims.

What is claimed is:

1. A computer-implemented method of detecting a non-semantic and paralinguistic event in an audio stream comprising:
   performing one or more pre-processing steps on the audio stream to generate an input audio sequence comprising a plurality of time-separated audio segments;
   generating, by a student model, an embedding for the plurality of time-separated audio segments, the student model having been trained using knowledge distillation applied to a self-supervised triplet loss embedding model, the self-supervised triplet loss embedding model having been trained to learn an audio feature set in a self-supervised triplet loss manner from a plurality of speech audio clips; and
   providing the embedding for the plurality of audio segments to an inference model performing inference to detect the non-semantic and paralinguistic event.

2. The method of claim 1, further comprising:
   detecting, by the inference model, the non-semantic and paralinguistic event; and
   generating one or more metrics for the non-semantic and paralinguistic event.

3. The method of claim 2, wherein the performing of the inference to detect the non-semantic and paralinguistic event occurs on a mobile device in substantial real-time.

4. The method of claim 1, wherein the performing of the inference to detect the non-semantic and paralinguistic event comprises a determination of whether the audio stream contains speech from a person wearing a mask.

5. The method of claim 1, wherein the non-semantic and paralinguistic event comprises one or more of crying, coughing, snoring, sneezing, wheezing, or a hiccup.

6. The method of claim 1, wherein the non-semantic and paralinguistic event comprises coughing, and further comprising:
   performing a cough-type classification to determine whether the cough comprises a wet cough, a dry cough, a cough associated with one or more of a respiratory tract infection, emphysema, exposure to smoke, exposure to air pollution, allergies, acid reflux, heart failure, or lung tumors.

7. The method of claim 1, further comprising:
   training the self-supervised triplet loss embedding model to learn the audio feature set in the self-supervised triplet loss manner from the plurality of speech audio clips from the speech dataset.

8. The method of claim 1, further comprising:
   training the student model based on a trained self-supervised triplet loss embedding model.

9. The method of claim 8, wherein the student model is further configured based on one or more of: (i) varying a number filters in each layer of the student model, (ii) reducing a size of a bottleneck layer kernel by computing a global average over pixels in each output feature map, (iii) applying a compression operator to a bottleneck layer, wherein the compression operator is based on a Singular Value Decomposition (SVD) that is configured to learn a low-rank approximation of a weight matrix associated with the bottleneck layer, or (iv) applying Quantization-Aware training (QAT) that is configured to gradually reduce a numerical precision of weights associated with a bottleneck layer during training.

10. The method of claim 1, wherein the generating of the embedding comprises utilizing temporal proximity in the plurality of speech audio clips as a self-supervision signal.

11. The method of claim 1, further comprising:
instructing a user generating the audio stream to conduct a calibration procedure in which the user is instructed to utter the non-semantic and paralinguistic event N times;
computing an embedding for each utterance of non-semantic and paralinguistic event using the audio feature set;
computing a similarity between each pairwise combination of the N utterances; and
determining a verification threshold for the inference model based on the computed similarities.

12. The method of claim 11, further comprising:
receiving user indication to detect one or more additional utterances of non-semantic and paralinguistic events over a time period;
initiating a recording of audio events during the time period;
terminating the recording of the audio events upon expiration of the time period; and
detecting the one or more additional utterances of non-semantic and paralinguistic events by comparing the recorded audio events with the N utterances.

13. The method of claim 12, further comprising:
receiving a second user indication to provide the detected one or more additional utterances of non-semantic and paralinguistic events to a designated healthcare provider; and
responsive to the second user indication, providing the detected one or more additional utterances of non-semantic and paralinguistic events to the designated healthcare provider.

14. A computing device for detecting a non-semantic and paralinguistic event in an audio stream comprising:
one or more processors operable to perform operations, the operations comprising:
performing one or more pre-processing steps on the audio stream to generate an input audio sequence comprising a plurality of time-separated audio segments;
generating, by a student model, an embedding for the plurality of time-separated audio segments, the student model having been trained using knowledge distillation applied to a self-supervised triplet loss embedding model, the self-supervised triplet loss embedding model having been trained to learn an audio feature set in a self-supervised triplet loss manner from a plurality of speech audio clips; and
providing the embedding for the plurality of audio segments to an inference model performing inference to detect the non-semantic and paralinguistic event.

15. The computing device of claim 14, wherein the computing device comprises one or more of a home intelligent assistant, a portable computer including a microphone for recording the audio stream, or a smartphone.

16. The computing device of claim 14, wherein the performing of the inference to detect the non-semantic and paralinguistic event occurs on the computing device in substantial real-time.

17. The computing device of claim 14, the operations further comprising:
training the self-supervised triplet loss embedding model to learn the audio feature set in the self-supervised triplet loss manner from the plurality of speech audio clips from the speech dataset.

18. The computing device of claim 14, the operations further comprising:
training the student model based on a trained self-supervised triplet loss embedding model.

19. The computing device of claim 14, the operations further comprising:
instructing a user generating the audio stream to conduct a calibration procedure in which the user is instructed to utter the non-semantic and paralinguistic event N times;
computing an embedding for each utterance of non-semantic and paralinguistic event using the audio feature set;
computing a similarity between each pairwise combination of the N utterances; and
determining a verification threshold for the inference model based on the computed similarities.

20. The computing device of claim 19, the operations further comprising:
receiving user indication to detect one or more additional utterances of non-semantic and paralinguistic events over a time period;
initiating a recording of audio events during the time period;
terminating the recording of the audio events upon expiration of the time period; and
detecting the one or more additional utterances of non-semantic and paralinguistic events by comparing the recorded audio events with the N utterances.

21. The computing device of claim 20, the operations further comprising:
receiving a second user indication to provide the detected one or more additional utterances of non-semantic and paralinguistic events to a designated healthcare provider; and
responsive to the second user indication, providing the detected one or more additional utterances of non-semantic and paralinguistic events to the designated healthcare provider.

22. One or more non-transitory computer-readable storage media for detecting a non-semantic and paralinguistic event in an audio stream comprising computer-executable instructions that, when executed by one or more processors, cause the one or more processors to perform operations comprising:
performing one or more pre-processing steps on the audio stream to generate an input audio sequence comprising a plurality of time-separated audio segments;
generating, by a student model, an embedding for the plurality of time-separated audio segments, the student model having been trained using knowledge distillation applied to a self-supervised triplet loss embedding model, the self-supervised triplet loss embedding model having been trained to learn an audio feature set in a self-supervised triplet loss manner from a plurality of speech audio clips; and
providing the embedding for the plurality of audio segments to an inference model performing inference to detect the non-semantic and paralinguistic event.

* * * * *